United States Patent [19]

Habermann et al.

[11] Patent Number: 5,496,924
[45] Date of Patent: Mar. 5, 1996

[54] FUSION PROTEIN COMPRISING AN INTERLEUKIN-2 FRAGMENT BALLAST PORTION

[75] Inventors: Paul Habermann, Taunus; Friedrich Wengenmayer, Hofheim am Taunus, both of Germany

[73] Assignee: Hoechst Aktiengesellschaft, Frankfurt am Main, Germany

[21] Appl. No.: 194,545

[22] Filed: Dec. 28, 1992

Related U.S. Application Data

[63] Continuation of Ser. No. 377,313, Jul. 10, 1989, abandoned, which is a continuation-in-part of Ser. No. 934,910, Nov. 25, 1986, abandoned, and Ser. No. 943,804, Dec. 19, 1986, abandoned.

[30] Foreign Application Priority Data

Nov. 27, 1985 [DE] Germany .......................... 35 41 856.7
Dec. 21, 1985 [DE] Germany .......................... 35 45 565.9
Oct. 30, 1986 [DE] Germany .......................... 36 36 903.9

[51] Int. Cl.$^6$ .......................... C07K 14/47; C07K 14/62; C07K 14/815; C07K 19/00
[52] U.S. Cl. .......................... 530/350; 530/303; 530/351
[58] Field of Search .......................... 530/350, 351, 530/399, 427, 303; 435/69.4, 69.7

[56] References Cited

U.S. PATENT DOCUMENTS

| H245 | 4/1987 | Bahl | 435/69.4 |
|---|---|---|---|
| 4,431,740 | 2/1984 | Bell et al. | 435/69.4 |
| 4,568,640 | 2/1986 | Rubin | 435/70 |
| 4,636,463 | 1/1987 | Altman et al. | 530/351 |
| 4,650,761 | 3/1987 | Hershberger et al. | 435/69.4 |
| 4,711,845 | 12/1987 | Gelfand et al. | 435/68 |
| 4,738,921 | 4/1988 | Belagaje et al. | 435/68 |
| 4,738,927 | 4/1988 | Taniguchi et al. | 530/351 |
| 4,784,949 | 11/1988 | Gelfand et al. | 435/172.3 |
| 4,914,026 | 4/1990 | Brake et al. | 435/69.4 |
| 4,935,233 | 6/1990 | Bell et al. | 530/351 |
| 5,227,293 | 7/1993 | Stengelin et al. | 435/69.7 |
| 5,298,603 | 3/1994 | Habermann et al. | 530/351 |
| 5,358,857 | 10/1994 | Stengelin et al. | 435/69.7 |
| 5,359,035 | 10/1994 | Habermann | 530/351 |

FOREIGN PATENT DOCUMENTS

| 43070/85 | 12/1985 | Australia . |
|---|---|---|
| 0091539 | 10/1983 | European Pat. Off. . |
| 0155655 | 9/1985 | European Pat. Off. . |
| 0158198 | 10/1985 | European Pat. Off. . |
| 0161937 | 11/1985 | European Pat. Off. . |
| 0195680 | 9/1986 | European Pat. Off. . |
| WO85/00817 | 2/1985 | WIPO . |
| 85/02200 | 5/1985 | WIPO . |

OTHER PUBLICATIONS

Clark et al., PNAS 81, 1984, pp. 2543–2547.
Cerretti et al., PNAS 83, 1986, pp. 3223–3227.
Senoo et al., CA 104, 1986, #220129e.
Wong et al., PNAS 83, 1986, pp. 3233–3237.
Robb et al., PNAS 80, 1983, pp. 5990–5994.
Ueda et al., CA, 106, 1987, #79659k.
Igarashi et al., CA, 107, 1987, #148599a.
JP 2185096 (abstract).

*Primary Examiner*—Stephen G. Walsh
*Attorney, Agent, or Firm*—Finnegan, Henderson, Farabow, Garrett & Dunner

[57] ABSTRACT

A fusion protein including a ballast portion and a desired protein. The ballast portion forms either the C- or N-terminus of the fusion protein, and the ballast portion includes a part of the amino acid sequence of interleukin-2 (IL-2). According to certain preferred embodiments, the ballast portion includes approximately the first 100 amino acids of IL-2. According to other preferred embodiments, the ballast portion contains fewer than 100 amino acids of IL-2. According to further advantageous embodiments, a synthetic IL-2 gene is divided by unique cleavage sites into 6 segments, any number of these segments can be linked in arbitrary sequence. These embodiments permit specific instructions with which the solubility of the fusion protein can be altered, and thus the fusion proteins can readily be separated from soluble proteins intrinsic to a host. The DNA coding for the fusion proteins, as well as vectors and hosts are also provided.

10 Claims, 25 Drawing Sheets

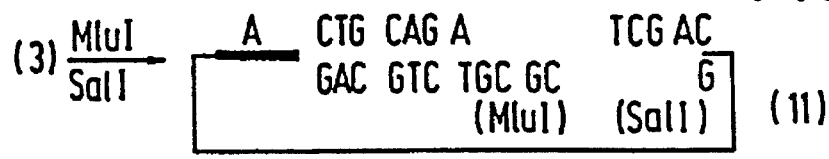
FIG.1
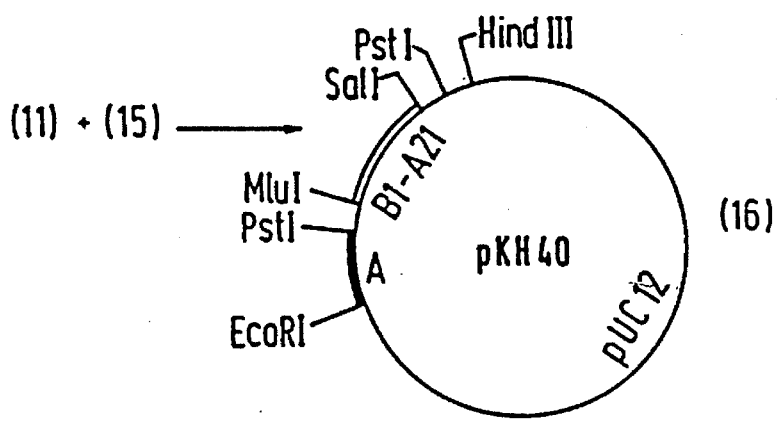
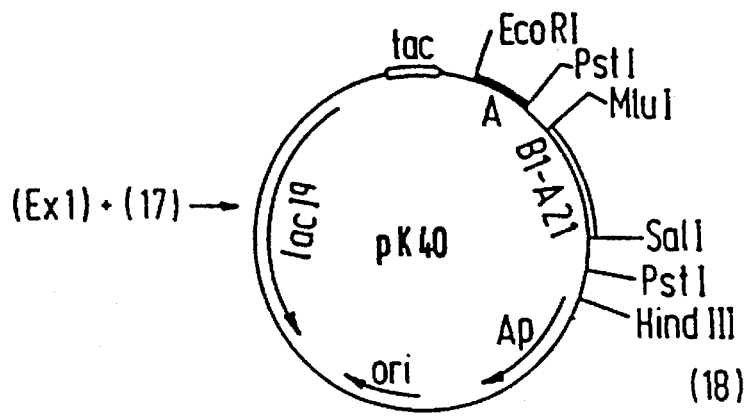

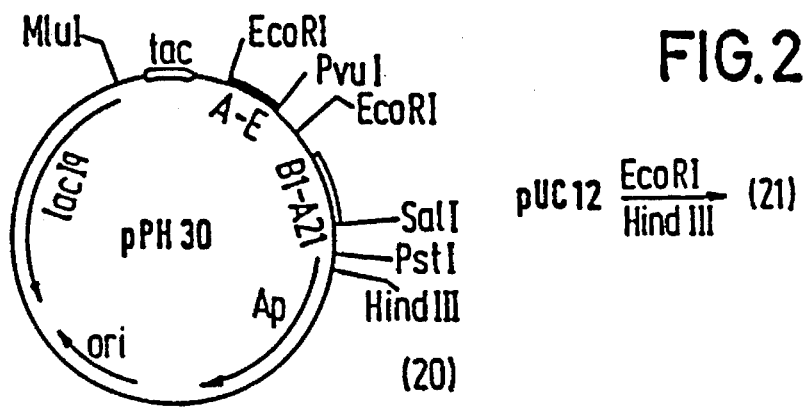

FIG.2

```
           EcoRI
113 114 ┌──────┐
Thr Ile Asp Phe  Met Ile Thr Thr Tyr Ser Leu Ala Ala Gly Arg
ACG ATC GAA TTC  ATG ATC ACA ACG TAT AGC TTG GCT GCA GGT CGC    (20a)
TGC TAG CTT AAG  TAC TAG TGT TGC ATA TCG AAC CGA CGT CCA GCG
└──────┘
  PvuI
```

(20) $\xrightarrow{\text{PvuI}/\text{HindIII}}$ (PvuI)-EcoRI ≠ B1-A21-SalI-Pst-(HindIII) (22)

(3) $\xrightarrow{\text{EcoRI}/\text{PvuI}}$ (EcoRI)-A-PstI-MluI-XbaI-SacI-(PvuI) (23)

(21) + (23) + (22) ⟶

(24) $\xrightarrow{\text{HindIII}/\text{EcoRI,part.}}$ (EcoRI)-A-PstI ≠ EcoRI ≠
-B1-A21-SalI-PstI-(HindIII)
(25)

(Ex1) + (25) ⟶

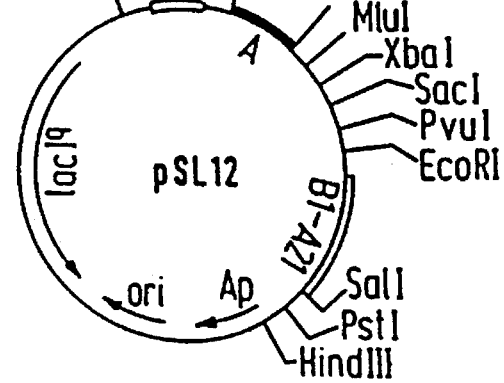

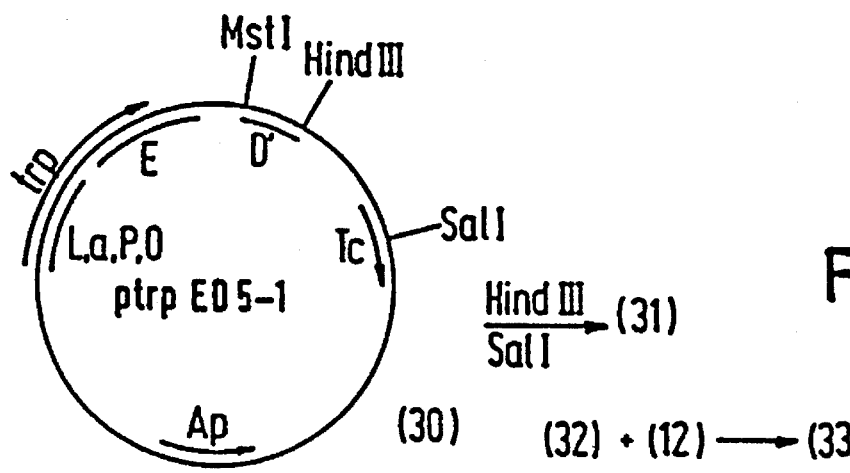
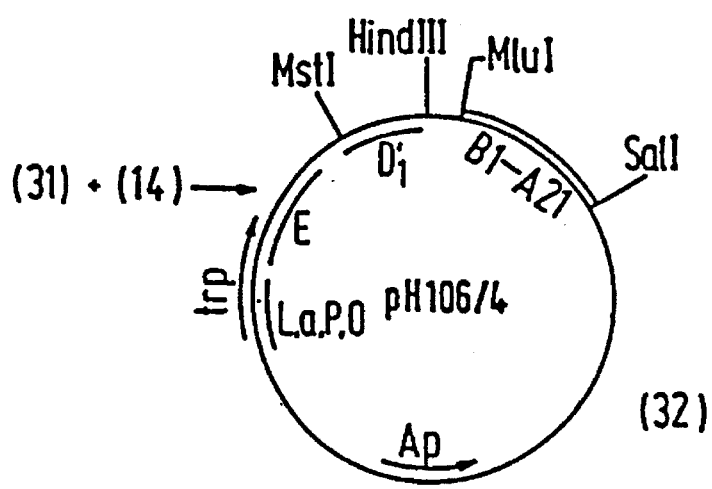
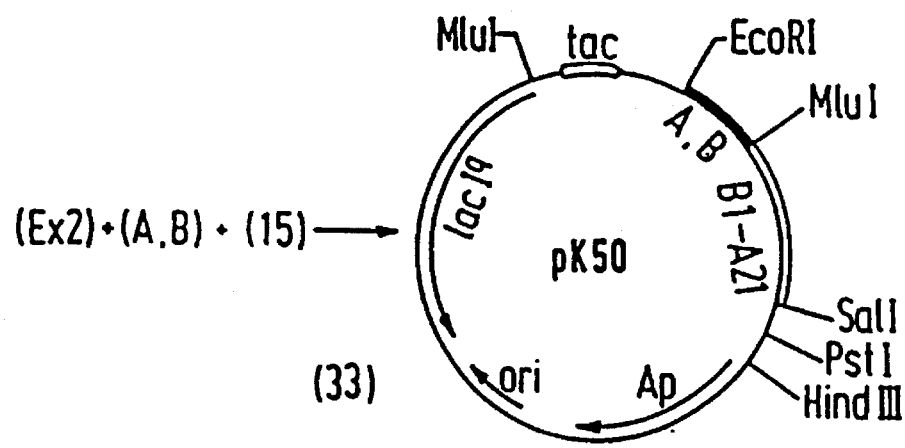
FIG. 3

FIG. 4
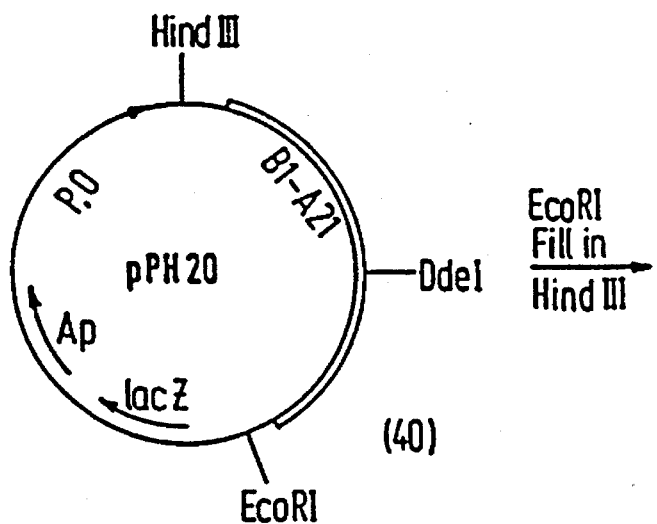
EcoRI
Fill in
―――――→
HindIII
(40)
```
(Ser)(Leu) Ala Ala Gly Arg         Stp Stp
     AGC TTG GCT GCA GGT CGC (B1-A21) TAA TAG TCG AGG GAA TT    (41)
         AC CGA CGT CCA GCG          ATT ATC AGC TCC CTT AA
     (HindIII)                                  (EcoRI⁻)
```
```
           38
       (Arg) Leu Gln Met Pro (Ser)
         CG CGT CTG CAG ATG CCA                (42)
            A GAC GTC TAC GGT TCG A
        (MluI)              (HindIII)
```
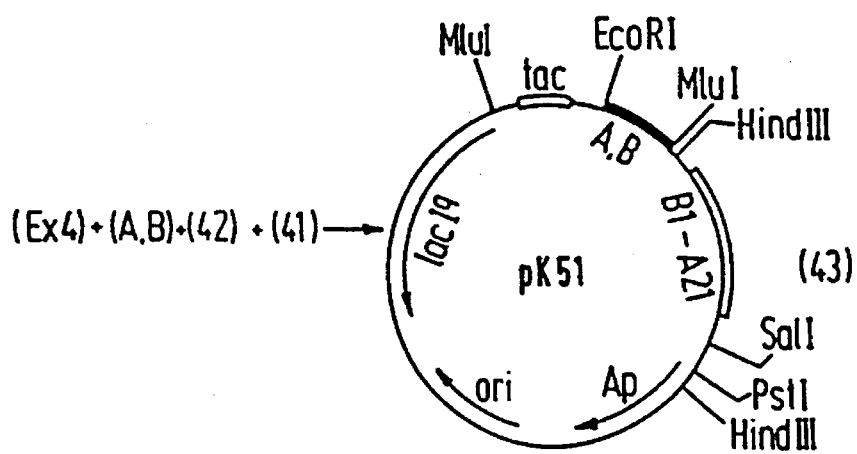
(Ex4)+(A.B)+(42)+(41) ⟶
(43)

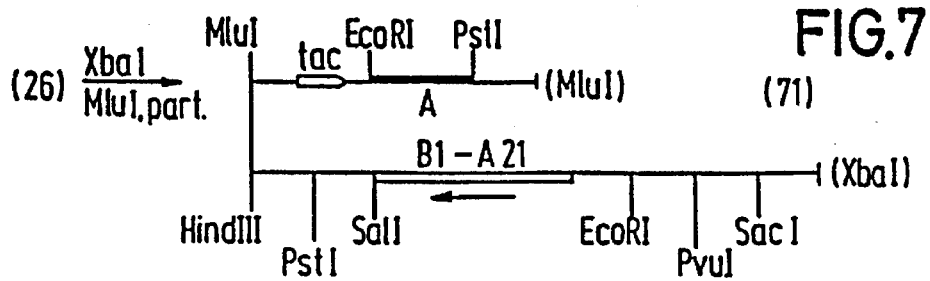
FIG. 7
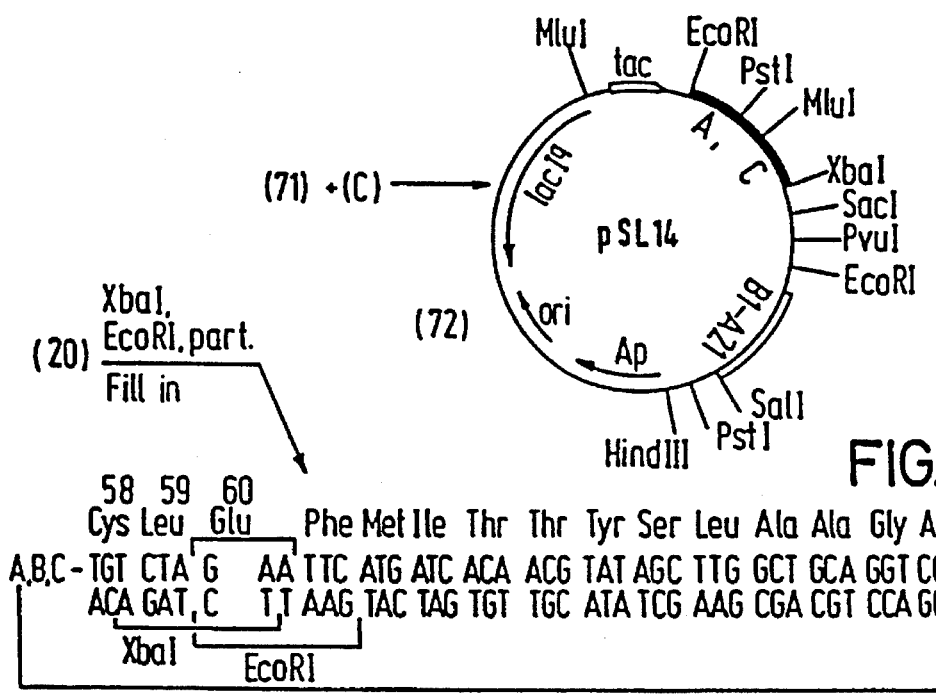
FIG. 8
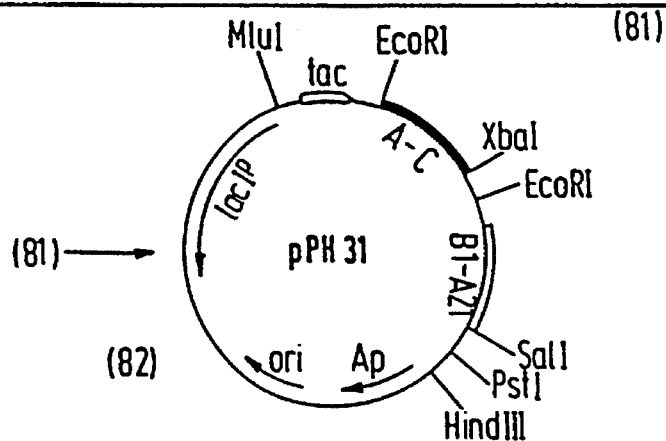

FIG. 9

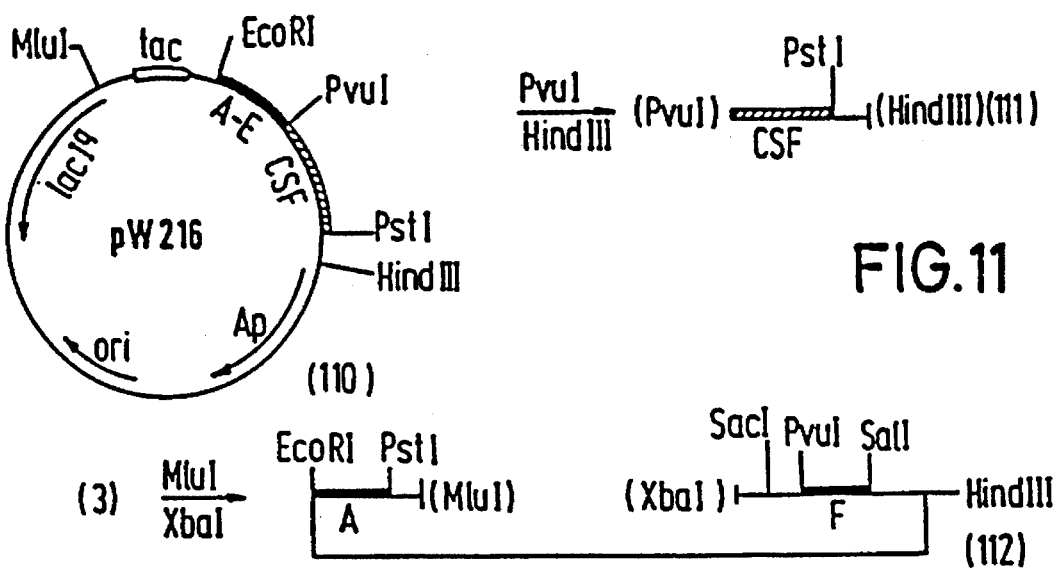
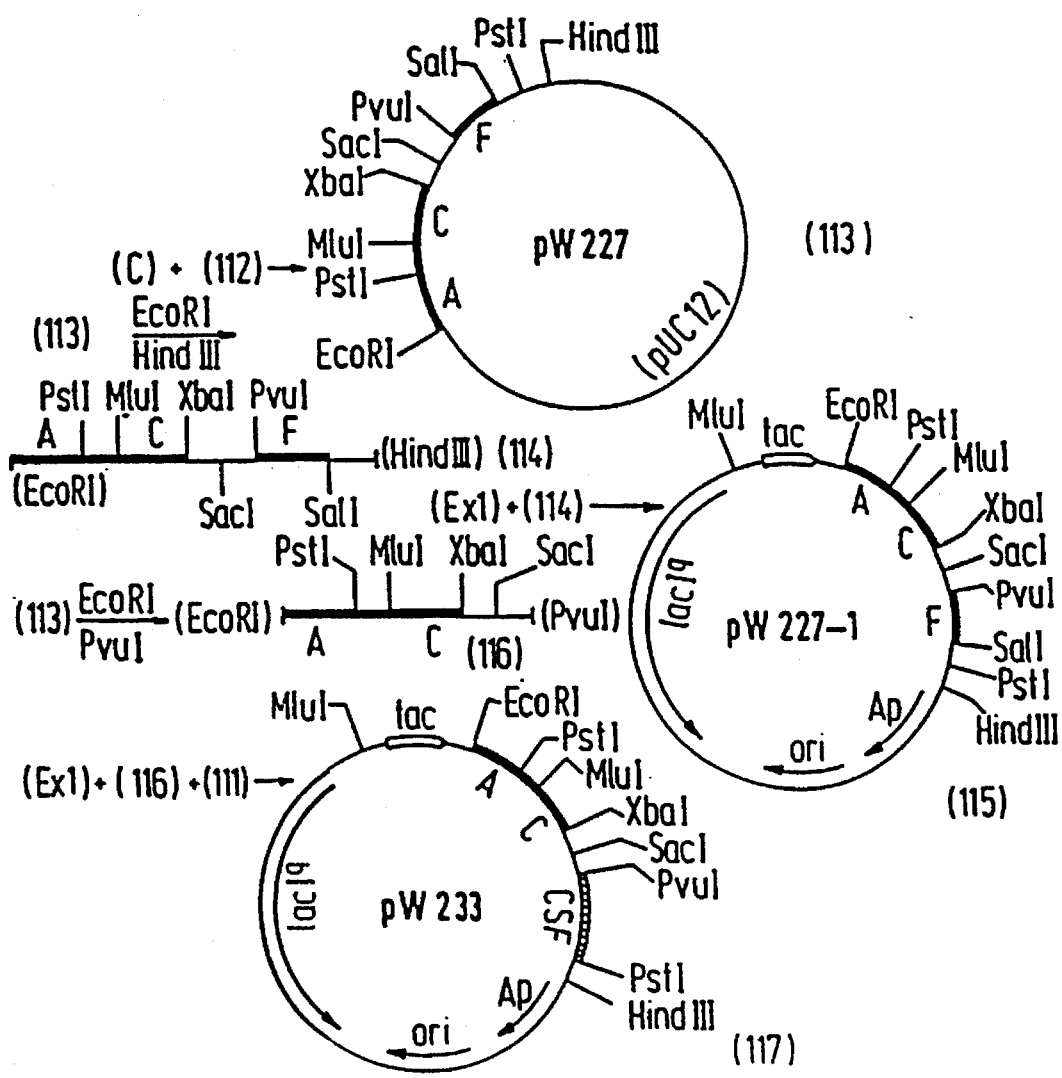
FIG. 11

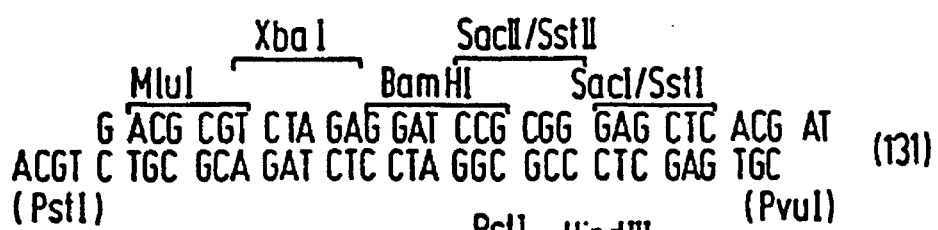
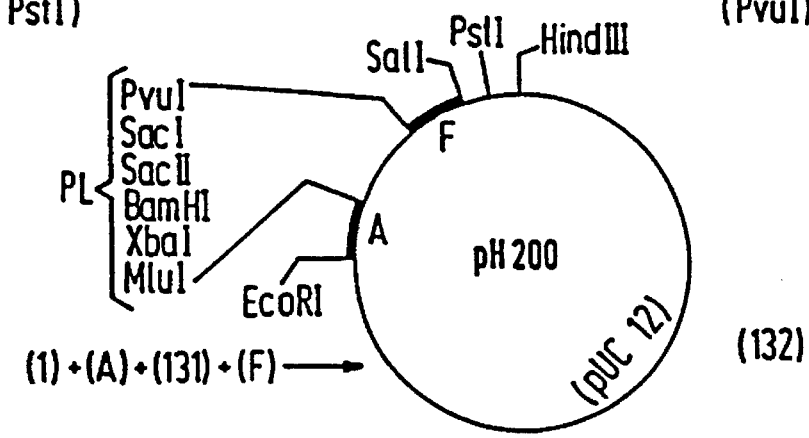
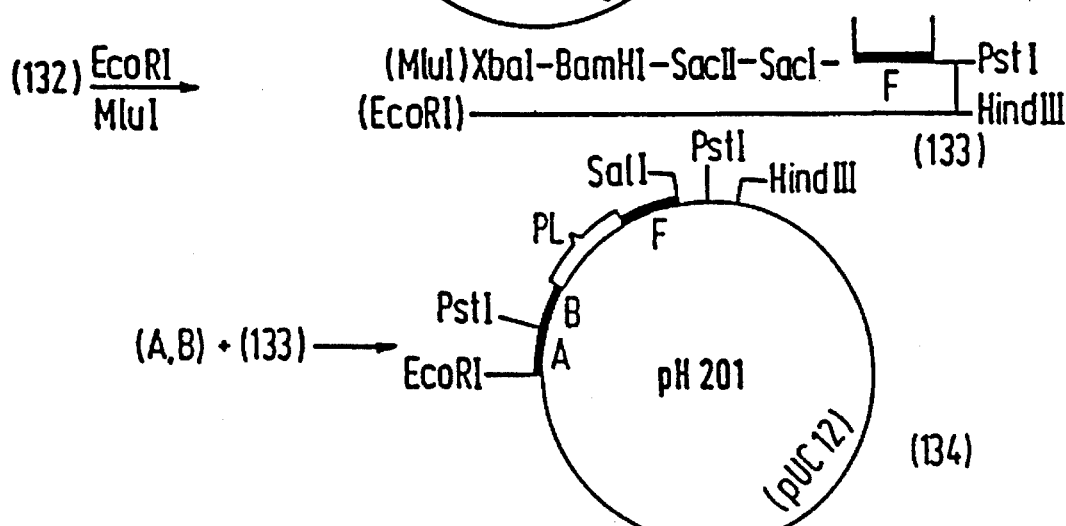
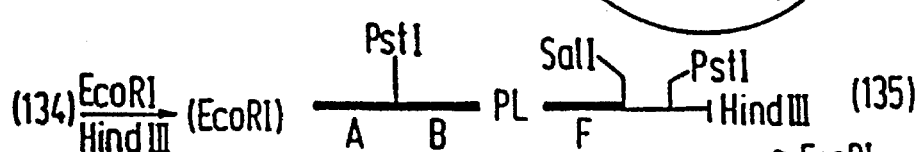
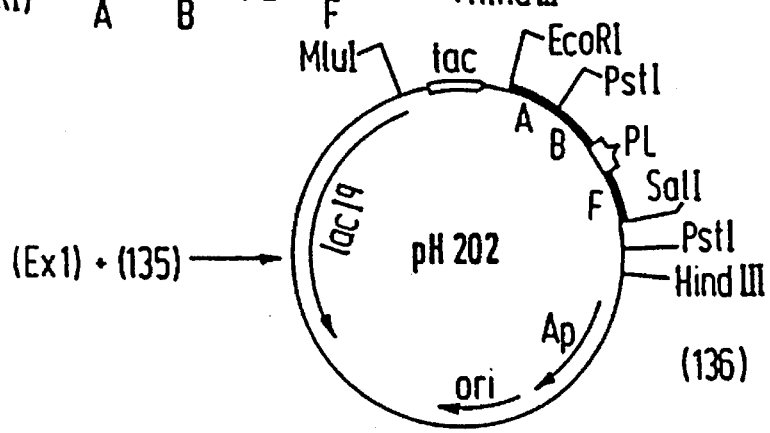
FIG. 13

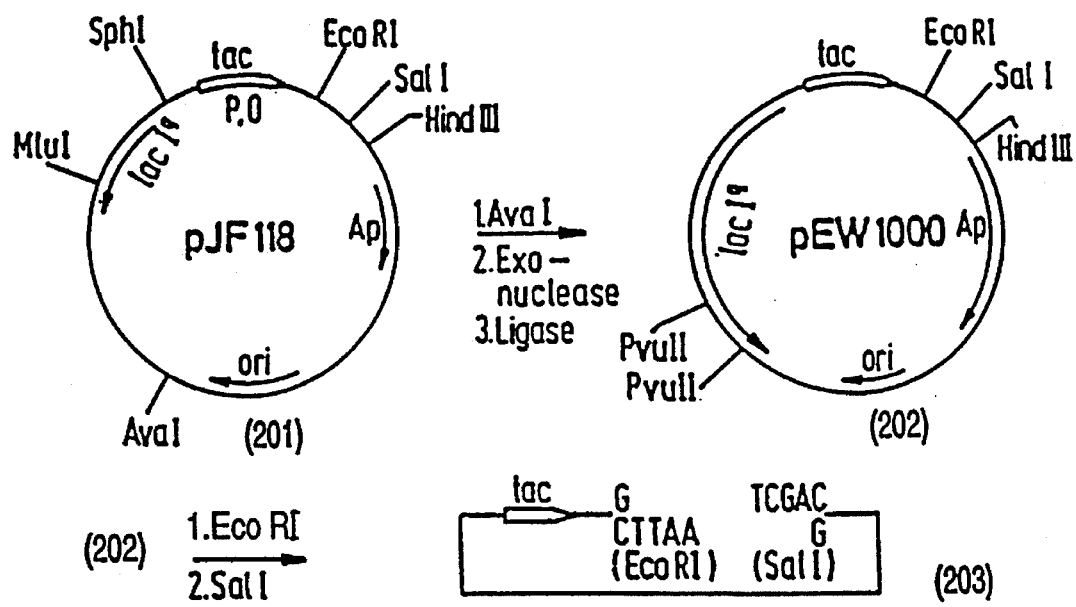
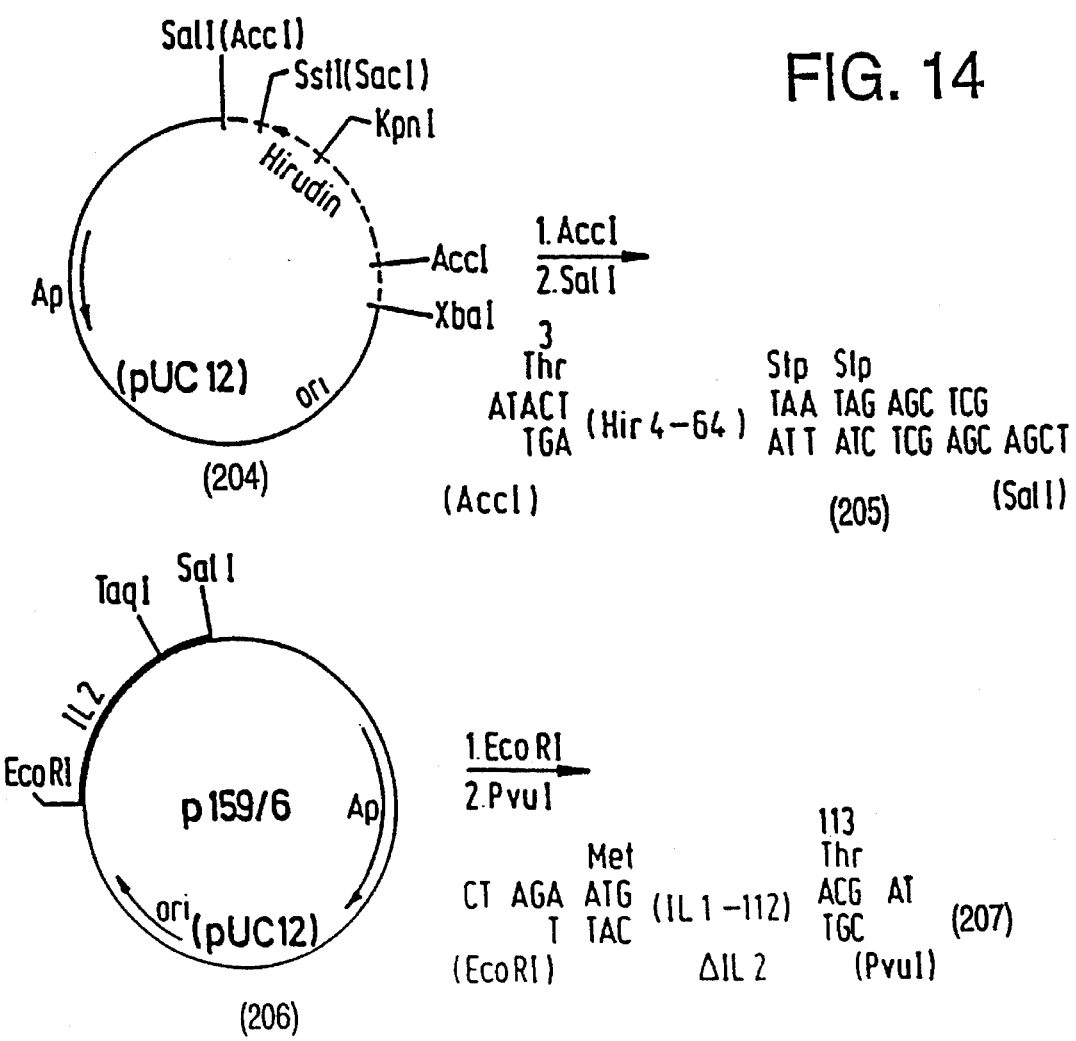
FIG. 14

FIG. 16a (221)+(222)+(223) →Ligase→ pPH 5 [plasmid: EcoRI, BamHI, B1–A15, Dde I, Pvu II, Ap, ori] (224)

(224) →BamHI/Pvu II→ GATCC/G (B1–A14) A15 CAG/GTC (225)
   (BamHI)            (Pvu II)

```
A16                      A21  Stp  Stp
CTG GAG AAC TAC TGC AAC  TAA  TAG
GAC CTC TTG ATG ACG TTG  ATT  ATC AGC T   (226)
(Pvu II)                                (Sal I)
``` pUC 8 →BamHI/Sal I→

```
       (Gly)
         G              TCGAC
    ┌ CCT AG                G ┐
    │  (BamHI)         (Sal I) │   (227)
```

(225)+(226)+(227) →Ligase→ pPH 15 [plasmid: BamHI, P.O, B1–A21, Dde I, Ap, lac Z, Pvu II, Sal I]  (228)

FIG. 16c

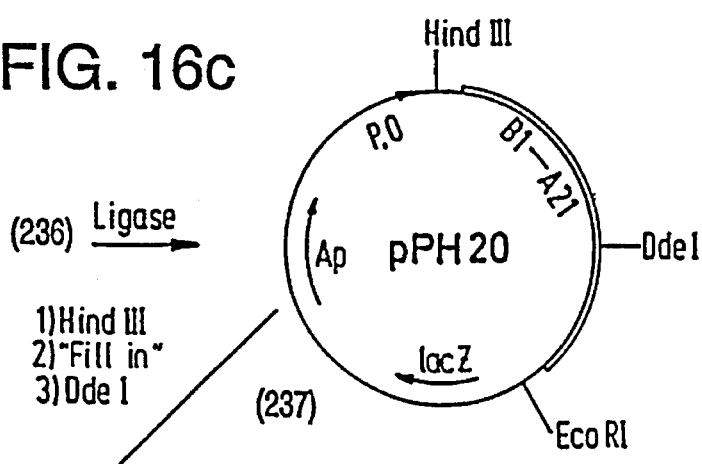

(236) Ligase →

1) Hind III
2) "Fill in"
3) Dde I (237)

```
        Ser Leu Ala Ala Gly Arg          CC
    AGC TTG GCT GCA GGT CGC (B1–C6)  GGA GT   (238)
    TCG AAC CGA CGT CCA GCG              (Dde I)
```

(228) SalI/DdeI →
```
            T CAG         Stp Stp
              C  (C9–A21) TAA TAG
                          ATT ATC  AGC T   (239)
          (Dde I)                   (Sal I)
```

(209) 1) Acc I  2) "Fill in"
      3) Eco RI. part. →

```
                         113 114    Eco RI
                         Thr Ile Asp Phe Met Ile Thr Thr Tyr
   AATTC ATG (IL1–112) ACG ATC GAA TTC ATG ATC ACA ACG TAT
       G TAC             TGC TAG CTT AAG TAC TAG TGT TGC ATA
   (Eco RI)                      Pvu I                    (240)
```

(203)+(238)+(239)+(240) Ligase →

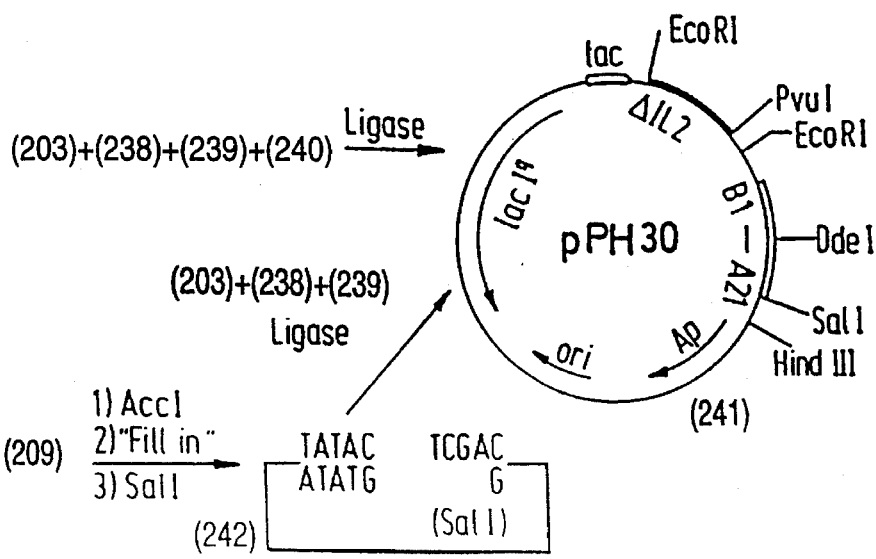

(203)+(238)+(239) Ligase (209) 1) Acc I
      2) "Fill in"  TATAC   TCGAC
      3) Sal I      ATATG      G
                           (Sal I)
      (242)

(257) $\frac{\text{Eco RI}}{\text{Hind III}}$ → EcoRI (IL1-96)—Y—(B1-A21)—Hind III (258)

Y=

| Ala | Gln | Phe | Met | Ile | Thr | Thr | Tyr | Ser | Leu | Ala | Ala | Gly | Arg |
|---|---|---|---|---|---|---|---|---|---|---|---|---|---|
| GCC | CAA | TTC | ATG | ATC | ACA | ACG | TAT | AGC | TTG | GCT | GCA | GGT | CGC |
| CGG | GTT | AAG | TAC | TAG | TGT | TGC | ATA | TCG | AAC | CGA | CGT | CCA | GCG |

(258)+(253) —Ligase→

FIG. 22
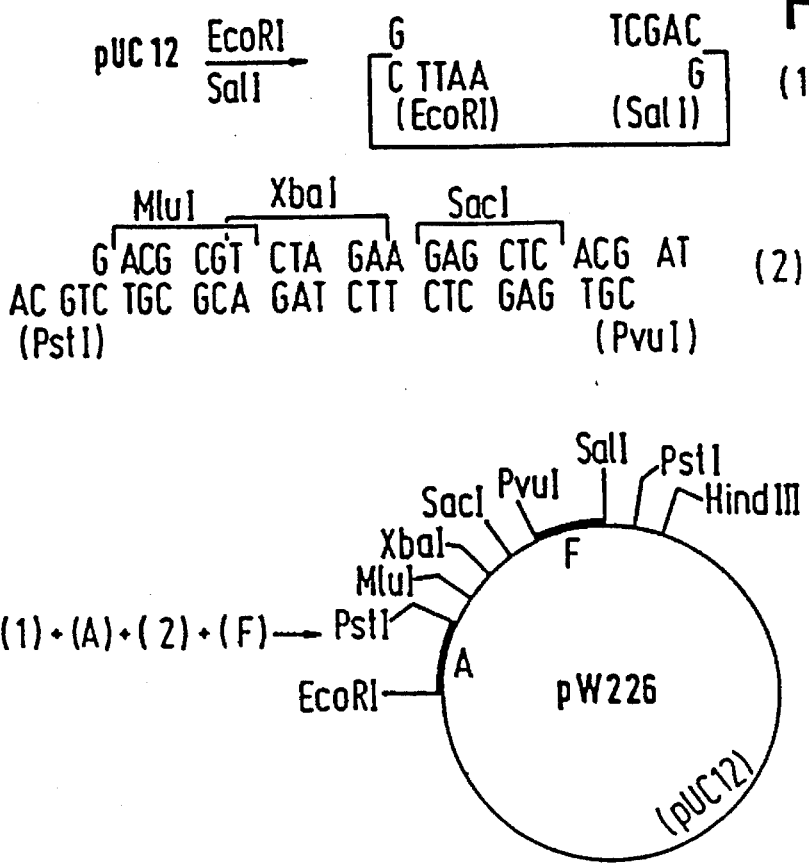
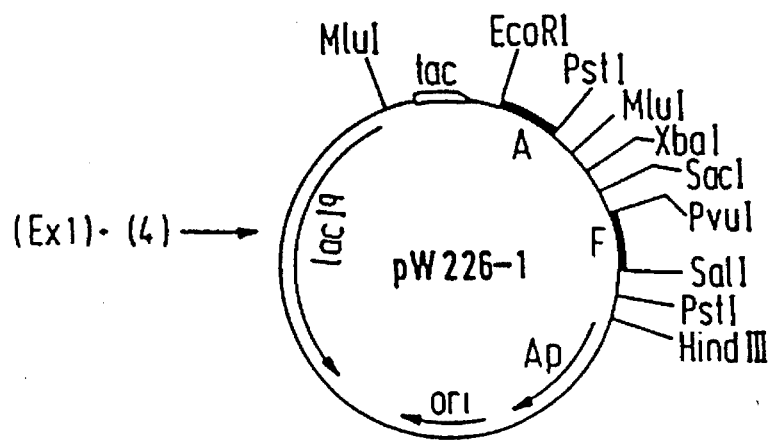

FUSION PROTEIN COMPRISING AN INTERLEUKIN-2 FRAGMENT BALLAST PORTION

This application is a continuation of application Ser. No. 07/377,313 filed Jul. 19, 1989, now abandoned, which was a continuation-in-part of application Ser. Nos. 06/934,910 and 06/943,804, filed Nov. 25, 1986 and Dec. 19, 1986, respectively both abandoned.

The invention relates to an "open reading frame" from a DNA which codes for interleukin-2, and to the use of this DNA as an aid for the expression of peptides and proteins.

In the preparation of eukaryotic proteins by genetic engineering, the yield obtained in bacteria is frequently low, especially in the case of small proteins which have a molecular weight up to about 15,000 Daltons and whose structures contain disulfide bridges. It is assumed that the proteins which have been produced are rapidly degraded by proteases intrinsic to the host. For this reason, it is expedient to construct gene structures using a fusion protein which is a protein intrinsic to the host and which, after isolation of the primary product, is cleaved off by methods known per se.

It has now been found, surprisingly, that an N-terminal section of interleukin-2 which essentially corresponds to the first 100 amino acids is especially well-suited for the preparation of fusion proteins. These proteins are surprisingly stable in the host cell. Thus, the primary product obtained is a fusion protein which is composed entirely or very predominantly of eukaryotic protein sequences. Surprisingly, this protein is apparently not recognized as foreign protein in the relevant host organism, nor is it immediately degraded again. Another advantage is that the fusion proteins according to the invention are sparingly soluble or insoluble and thus can straightforwardly and expediently be removed from the soluble proteins intrinsic to the host by centrifugation.

It is unimportant according to the invention for the fusion protein to have an interleukin-2 section (the ballast portion) which represents a biologically active molecule. Nor is the exact structure of the interleukin-2 section of importance. For this purpose, according to certain preferred embodiments, it is sufficient that essentially the first 100 N-terminal amino acids be present. Thus, it is possible, for example, to undertake at the N-terminal end modifications which allow cleavage of the fusion protein if the desired protein is located N-terminal thereto. Conversely, it is possible to undertake C-terminal modifications in order to make it possible or easier to cleave off the desired protein, if as is customary, the latter is C-terminal bonded in the fusion protein.

The natural DNA sequence coding for human interleukin-2, "IL-2" in the text which follows, is known from European Patent Application EP-A1-0,921,539. The literature cited there also relates to mammalian IL-2 DNA from mice and rats, which can be used for the synthesis of the proteins according to the invention, and IL-2 derived from human can preferably be used. However, it is more expedient to start from a synthetic DNA, and especially advantageously from the DNA for human IL-2 which has been proposed in the (non-prior published) German Offenlegungsschrift 3,419,995 (corresponding to European Patent Application 0,163,249). This synthetic DNA sequence is depicted in Table 1 (DNA sequence I) (appended hereto, before the claims). This synthetic DNA not only has the advantage that its choice of codons is suited to the circumstances in the host which is used most often, *E. coli*, but it also contains a number of cleavage sites for restriction endonucleases which can be utilized according to the invention.

Table 2 which follows gives a selection of the suitable cleavage sites at the start and in the region of the 100th triplet. However, this does not rule out the possibility of undertaking modifications in DNA in the intermediate region, it being possible to make use of the other cleavage sites listed in the above-mentioned patent application.

| Restriction enzyme | Recognition sequence | Position of the first nucleotide of the recognition sequence (coding strand) |
|---|---|---|
| Aha II, Ban I, HaeII, Nar I, Ban II, SacI, | 5' GGCGCC | 3' 8 |
| Sst I | GAGCTC | 291 |
| Hha I | GCGC | 9 |
| Hinf I | GACTC | 35 |
| PvuI | CGATCG | 346 |
| Taq I | TCGA | 387 |

If use is made of the nucleases Ban II, SacI or Sst I then an IL-2 part-sequence which codes for about 95 amino acids is obtained. This length is generally sufficient to obtain an insoluble fusion protein. If the solubility is still insufficiently low, for example in the case of a desired hydrophilic eukaryotic protein, but it is not intended to make use of the cleavage sites located nearer to the C-terminal end—in order to produce as little "ballast" as possible—then it is possible to extend the DNA sequence at the N- and/or C-terminal end by appropriate adaptors or linkers, and thus "tailor" the "ballast" section. It is also possible to use the DNA sequence—more or less —right up to the end and thus generate IL-2 which is biologically active, and optionally modified, as a "by-product" or generate a bifunctional protein which has the action of IL-2 in addition to the action of the coded protein.

Thus the invention relates to fusion proteins of the general formulae:

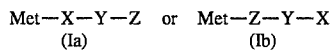

in which

X essentially denotes the amino acid sequence of approximately the first 100 amino acids of, preferably, human IL-2;

Y denotes a direct bond if the amino acid sequence adjacent to the desired protein allows the desired protein to be cleaved off, or otherwise denotes a bridging element which is composed of one or more genetically codable amino acids and permits cleavage; and Z is a sequence of genetically codable amino acids representing the desired protein.

As is evident from the formulae Ia and Ib—and as has already been mentioned above—it is possible to bring about the expression of the desired protein upstream or downstream of the IL-2 section. For simplicity in the following text, essentially the first option, which corresponds to the conventional method for the preparation of fusion proteins, will be illustrated. Thus, although this "classic" variant is described below, this is not intended to rule out the other alternative.

In a further development of this inventive concept, it has now been found, surprisingly, that even considerably smaller portions of the interleukin-2 molecule are suitable as "ballast" portion for fusion proteins of this type. The invention is defined in the patent claims. Preferred embodiments are explained in detail hereinafter.

It is particularly advantageous to start from the synthetic gene for IL-2 which is described in EP-A 0,163,249 and depicted in Table I. This synthetic gene contains a number of unique restriction cleavage sites which permit the DNA coding for IL-2 to be broken down into "manageable" segments. Using these segments it is possible by the modular principle to tailor the ballast portion for fusion proteins; the solubility of the fusion proteins obtained ranging from high to low depending on the combination of the segments and depending on the nature of the desired protein.

Thus, the invention allows the solubility to be directed towards that which is most advantageous for the possible or desired working up of the product. That is to say, it is directed to high solubility when the product is to be purified by chromatography, for example, using an antibody column, or directed to low solubility if, for pre-purification, the soluble proteins intrinsic to the host are to be removed, for example, by centrifugation.

A particular advantage of the invention is that it is possible to prepare fusion proteins having a very small "ballast portion", since this results in the relative yield of desired protein being considerably increased.

Another advantage of the invention is that the "ballast portion" can be constructed in such a way that it impairs the spatial structure of the desired protein as little as possible and thus, for example, does not prevent folding up.

Cleavage of the fusion proteins results in not only the desired protein but also the "ballast portion", that is to say the IL-2 derivative. This may have IL-2 activity (T-cell proliferation test) or bind to IL-2 receptors. The "modular principle" according to the invention can thus also be used to produce IL-2 derivatives as "by-products" which have the biological activities of IL-2 to a greater or lesser extent.

Particularly advantageous embodiments of the invention are explained hereinafter with reference to the synthetic gene described in EP-A 0,163,249. This gene is cut at the 5' end with the restriction endonuclease EcoRI and at the 3' end with SalI. Apart from the three unique restriction cleavage sites for the enzymes PstI, XbaI and SacI, which were used to construct this gene, the locations of the unique cleavage sites for MluI and PvuI are also favorable. When the sequences located between these cleavage sites are designated A to F, the synthetic gene can be represented diagrammatically as follows:

(EcoRI)-A-PstI-B-MluI-C-XbaI-D-SacI-E-PvuI-F-(SalI)

The segments A to F are thus particularly suitable "units" for the modular system according to the invention. Thus, in this representation the "ballast portion" for the fusion proteins described in German Patent Application P 3,541,856.7 corresponds to the segments A to E, and that for the bifunctional protein having the entire IL-2 gene, which is mentioned in the same application, corresponds to all the segments A to F. In contrast, the gene constructs according to the invention relate to other combinations of the segments, A to F, and according to certain embodiments preferably having fewer than four of these segments, the segment A coding for the N-terminal end of the fusion protein. The arrangement of the other segments is arbitrary, optional use being made of appropriate adaptors, linkers or bridging elements. Appropriate adaptor or linker sequences can also be introduced at the C-terminal end of the "ballast portion", and in this case they can code for amino acids or short amino acid sequences which permit or facilitate the cleavage, enzymatically or chemically, of the "ballast portion" from the desired protein. The adaptor or linker sequences can, of course, also be used to tailor the "ballast portion" for a particular fusion protein, for example, to achieve a desired solubility. In this context, it has emerged, surprisingly, that the solubility of the fusion proteins does not depend on the molecular size but that, on the contrary, even relatively small molecules may have low solubility. Thus, with knowledge of these relationships, which are explained in detail in the examples, those skilled in the art are able without great experimental effort to obtain fusion proteins according to the invention with a small "ballast portion" and having particular desired properties.

Thus, if the desired protein is a eukaryotic protein, the fusion proteins obtained according to the invention are composed exclusively or virtually exclusively of eukaryotic protein sequences. However, surprisingly, these fusion proteins are not recognized as foreign proteins by the prokaryotic host cells, and are not rapidly degraded by proteases intrinsic to the host. This degradation takes place particularly often in the case of proteins which are foreign to the host and coded for by cDNA sequences which are to be expressed in bacteria. It has now emerged that cDNA sequences can be expressed very effectively if they are "embedded" in the segments according to the invention. It is possible to construct specific vectors for this purpose, which contain polylinker sequences having several cloning sites for the cDNA sequences between the sequences according to the invention. Where the cDNA which has been cloned in to the segment contains no stop codon the polypeptide sequence coded for by the cDNA sequence is additionally protected by the polypeptide for which the C-terminal segment codes.

The fusion proteins can be cleaved chemically or enzymatically in a manner known per se. The choice of the suitable method depends, in particular, on the amino acid sequence of the desired protein. If the latter contains, for example, no methionine it is possible for Y or the connecting element to denote Met, in which case chemical cleavage with cyanogen chloride or bromide is carried out. If there is a cysteine at the carboxyl terminal end of Y or the connecting element, or if Y or the connecting element represents Cys, then it is possible to carry out a cysteine-specific enzymatic cleavage or chemical cleavage, for example after specific S-cyanylation. If there is a tryptophan at the carboxyl terminal end of Y or the connecting element, or if Y or the connecting element represents Trp, then chemical cleavage with N-bromosuccinimide can be carried out.

Desired proteins which do not contain Asp - Pro in their amino acid sequence and which are sufficiently stable to acid can, as fusion proteins with this bridging element, be cleaved proteolytically in a manner known per se. This results in proteins which contain N-terminal proline or C-terminal aspartic acid. It is therefore also possible in this way to synthesize modified proteins.

The Asp-Pro bond can be made even more labile to acid if this bridging element is $(Asp)_n$-Pro or Glu-$(Asp)_n$-Pro, n denoting 1 to 3.

Examples of enzymatic cleavages are likewise known, it also being possible to use modified enzymes of improved specificity (cf. C. S. Craik et al., Science 228 (1985) 291–297). If the desired eukaryotic peptide is proinsulin, then the chosen sequence for Y or the connecting element is advantageously a peptide sequence in which an amino acid, which can be split off with trypsin (Arg, Lys), is bonded to the N-terminal amino acid (Phe) of proinsulin, for example Ala-Ser-Met-Thr-Arg, since in this case, the arginine-specific cleavage can be carried out with the protease trypsin.

If the desired protein does not contain the amino acid sequence:

Ile-Glu-Gly-Arg, then the fusion protein with the appropriate bridging element can be cleaved with factor Xa (EP-A Publication Nos. 0,025,190 and 0,161,973).

The fusion protein is obtained by expression in a suitable expression system in a manner known per se. All known host-vector systems are suitable for this purpose as for example, mammalian cells and microorganisms, yeasts and preferably, bacteria, in particular E. coli.

The DNA sequence which codes for the desired protein is incorporated in a known manner into a vector which ensures satisfactory expression in the selected expression system.

In bacterial hosts, it is advantageous to select the promoter and operator from the group comprising lac, tac, trp, $P_L$ or $P_R$ of phage $\lambda$, hsp, omp or a synthetic promoter as proposed in, for example, German Offenlegungsschrift 3,430,683 (EP-A 0,173,149). The tac promoter-operator sequence is advantageous and is now commercially available (for example, expression vector pKK223-3, Pharmacia, "Molecular Biologicals, Chemicals and Equipment for Molecular Biology", 1984, page 63).

In the expression of the fusion protein according to the invention, it may prove advantageous to modify at least some of the individual triplets for the first few amino acids downstream of the ATG start codon in order to prevent any base-pairing at the mRNA level. Modifications of this type, as well as modifications, deletions or additions of individual amino acids in the IL-2 protein portion, are familiar to those skilled in the art, and the invention likewise relates to them. Elimination of cysteine or replacement of cysteine by other amino acids, in order to prevent formation of undesired disulfide bridges, as is disclosed in, for example, EP-A 109,748, may be mentioned by way of example.

The invention is illustrated in detail in the examples which follow and in the following figures.

BRIEF DESCRIPTION OF THE DRAWING FIGURES

FIGS. 1 to 17 illustrate in the manner of a flow diagram the processes of the synthesis described in the examples having the same numbers. To facilitate comprehension, the preparation of the starting materials and intermediates has been depicted in FIGS. 20 to 22. For the sake of clarity, the reference numbers in FIGS. 1 to 13 each start a new decade, thus (11) in FIG. 1. Reference numbers of starting materials to which the present application does not relate end with zero, thus, for example (20) in FIG. 2. The figures are not drawn to scale, in particular the scale is expanded appropriately in the region of the polylinker sequences. IL-2 sequences are defined by thick lines, and structural genes for desired proteins are emphasized in other ways.

FIG. 20 gives an overview of the segments A to F according to the invention and of the combination of segments A and B. The starting material is the plasmid p159/6, whose preparation is described in detail in EP-A 0,163,249 and which is defined by FIG. 5 in this publication.

FIG. 22 shows the preparation of the pUC12 derivative pW226 and of the expression plasmid pW226-1, both of which contain segments A and F separated by a polylinker sequence.

FIG. 1 shows the preparation of the pUC12 derivative pKH40 and of the expression plasmid pK40, which code for fusion proteins in which the protein sequence corresponding to sequence A, that is to say the first 22 amino acids of IL-2, is followed by the bridging element Thr-Arg, and subsequently with the amino acid sequence of proinsulin.

FIG. 2 shows the construction of the plasmid pSL11 and of the expression plasmid pSL12, which code for polypeptides in which the segment A is followed by a bridging element corresponding to polylinker sequences (2) and (20a), and subsequently the amino acid sequence of proinsulin.

FIG. 3 shows the construction of the expression plasmid pK50 which codes for a polypeptide in which segments A and B, that is to say the first 38 amino acids of IL-2, are directly followed by the amino acid sequence of proinsulin.

FIG. 4 shows the construction of the expression plasmid pK51 which codes for a polypeptide in which segments A and B are followed by a bridging element corresponding to sequences (42) and (41), to which is connected the amino acid sequence of proinsulin.

FIG. 7 shows the construction of the expression plasmid pSL14 from pSL12 (FIG. 2) by introduction of the fragment C into the polylinker. This results in direct attachment of the segment C to the segment A. In the following polylinker the first two amino acids (each Glu) correspond to amino acids 60 and 61 of IL-2. Thus, the IL-2 portion is composed of amino acids 1 to 22 and 37 to 61. The subsequent amino acid sequence corresponds to that which is coded for by the plasmid pSL12 (FIG. 2).

FIG. 8 shows the construction of the expression plasmid pPH31 which codes for a fusion protein in which segments A to C are followed by a bridging element which is represented by sequence (81), with subsequently the amino acid sequence of proinsulin.

Figure 9:
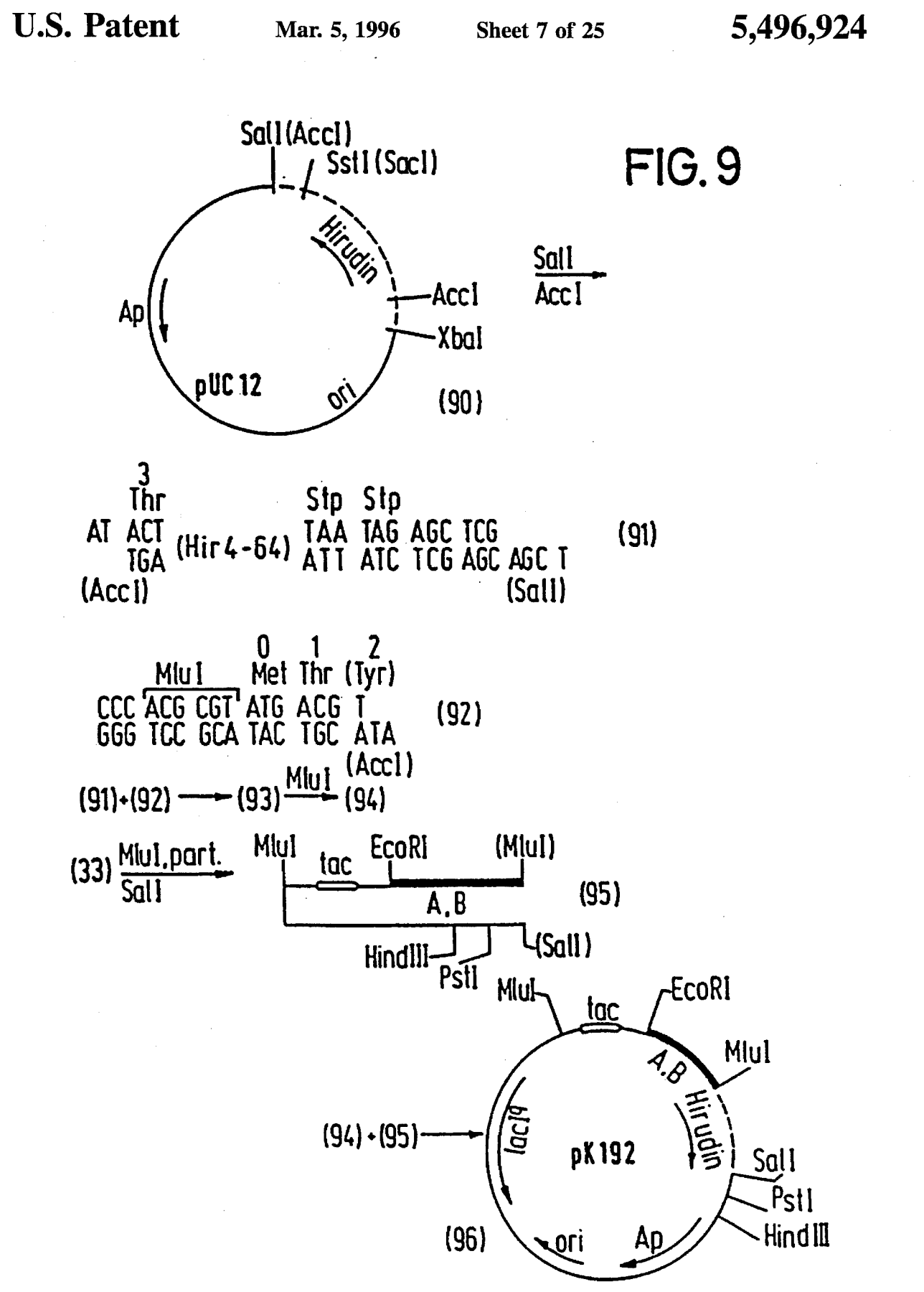

FIG. 9 shows the construction of the plasmid pK192 which codes for a fusion protein in which segments A and B are followed by methionine and, thereafter, the amino acid sequence of hirudin.

Figure 10:
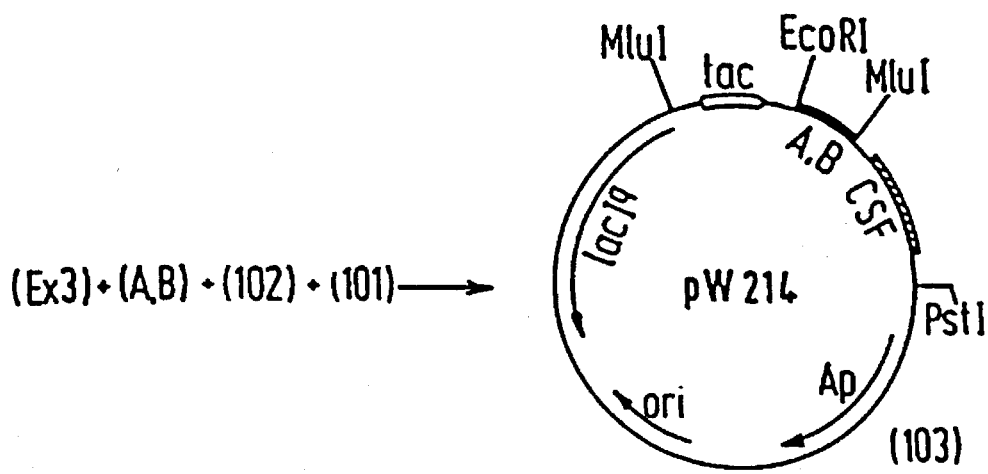

FIG. 10 shows the construction of the plasmid pW214 which codes for a fusion protein in which segments A and B are followed by the amino acid sequence which permits cleavage with factor Xa, with subsequently the amino acid sequence of granulocyte/macrophage colony stimulating factor (CSF).

FIG. 11 shows the construction of the expression plasmid pW233 which codes for a fusion protein in which segments A and C (corresponding to amino acids 1 to 22 and 37 to 61 of IL-2) are followed by the bridging element Leu-Thr-Ile-Asp-Asp-Pro, with subsequently the amino acid sequence of CSF.

Figure 12:
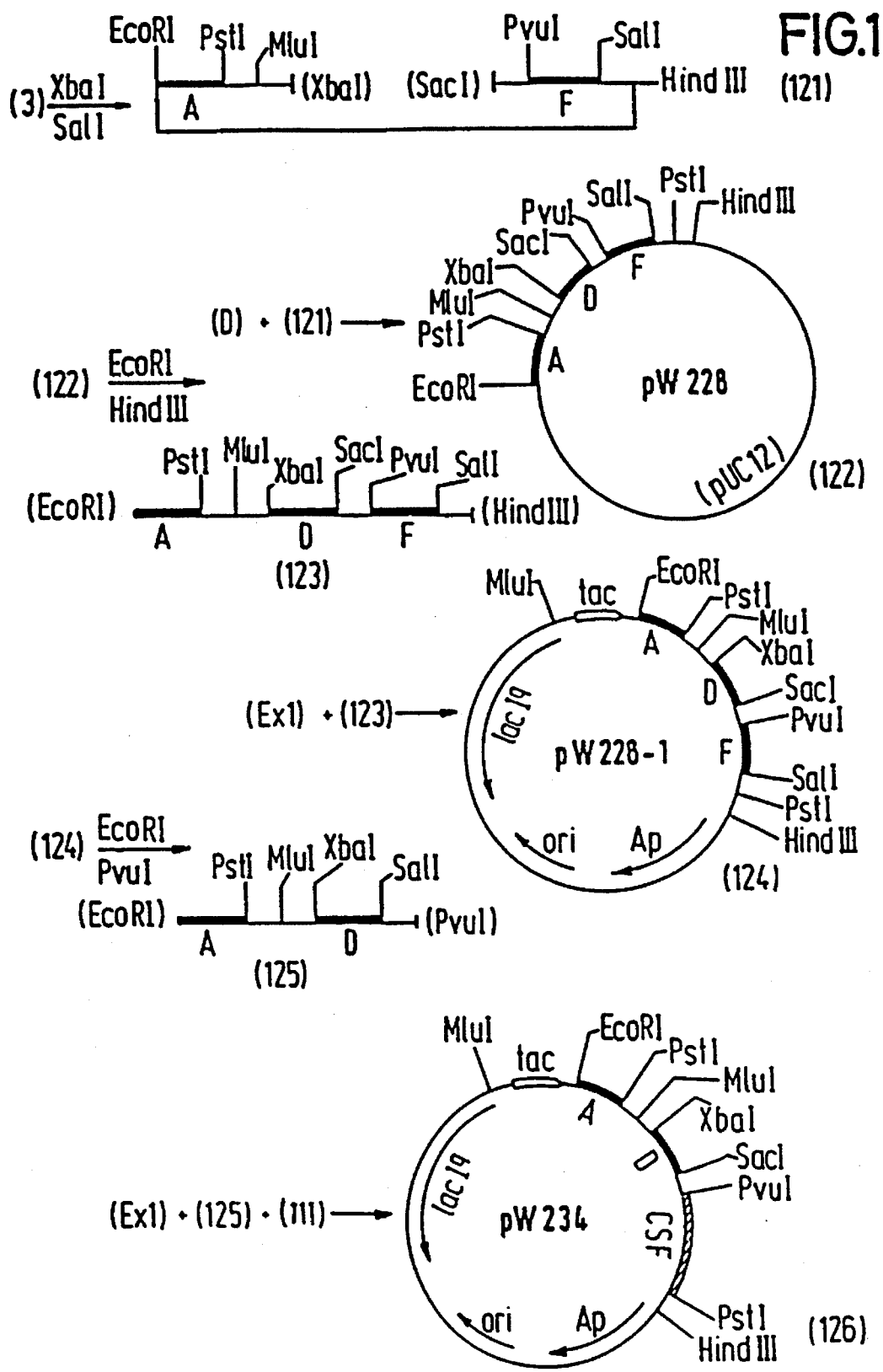

FIG. 12 shows the construction of the expression plasmid pW234 which codes for a fusion protein having the following amino acid sequence: Segment A (amino acids 1 to 22) is followed by a bridging element Thr-Arg, then by segment D (amino acids 59 to 96 of IL-2), by Thr-Asp-Asp-Pro as a further connecting element, and finally by CSF.

FIG. 13 shows the construction of the plasmids pH200 and pH201 and of the expression plasmid pH202. These plasmids have a polylinker located between segments A and F or A, B and F, into whose numerous cleavage sites foreign DNA can be cloned. These plasmids are particularly suitable for cloning cDNA sequences.

Figure 14A:
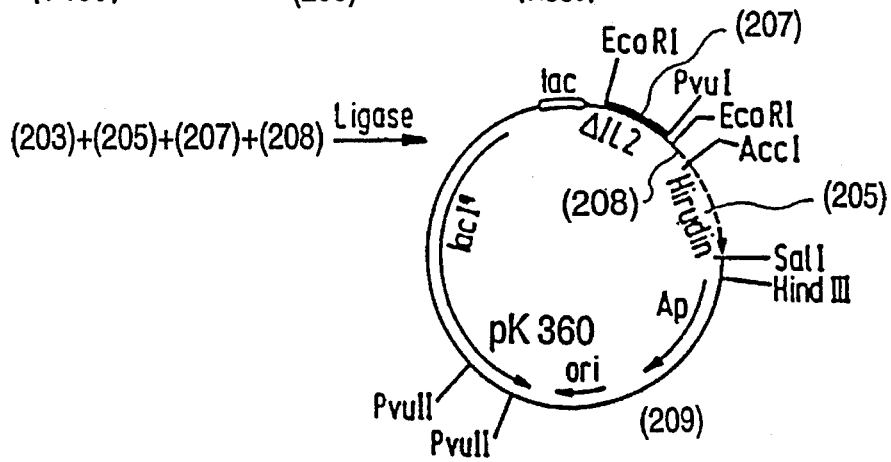

FIG. 14, and its continuation FIG. 14a, relate to the synthesis of the plasmid pK360 which codes for a fusion protein which has the hirudin sequence.

Figure 15:
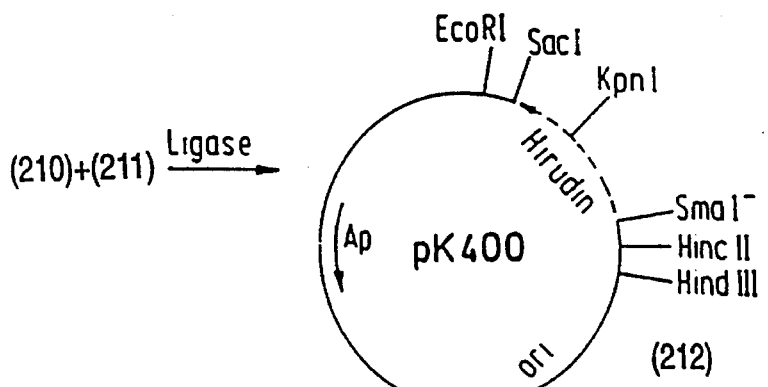
Figure 15A:
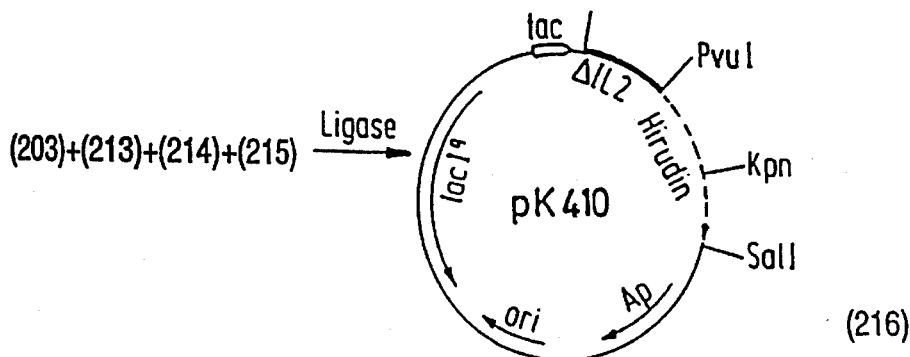

FIG. 15, and its continuation FIG. 15a, relate to the synthesis of the plasmid pK410 which likewise codes for a fusion protein having amino acid sequence of hirudin.

Figure 16:
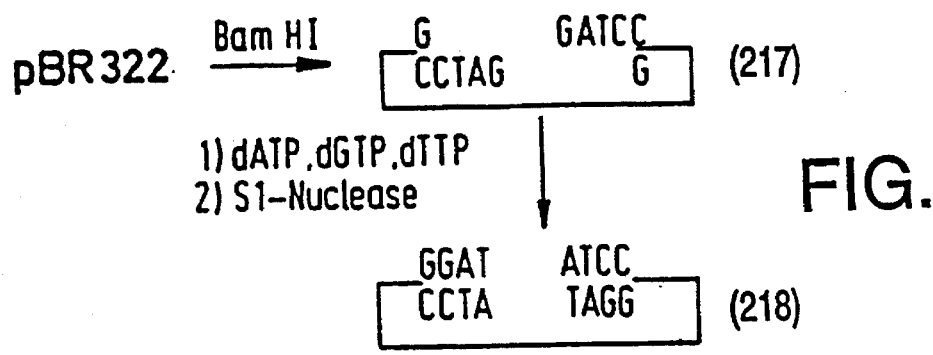
Figure 16B:
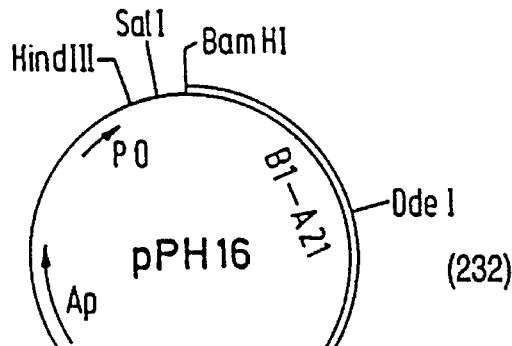

FIG. 16, and its continuations FIGS. 16a to 16c, relate to the construction of the plasmids pPH15, 16, 20 and 30 which code for fusion proteins which contain the amino acid sequence of monkey proinsulin.

Figure 17:
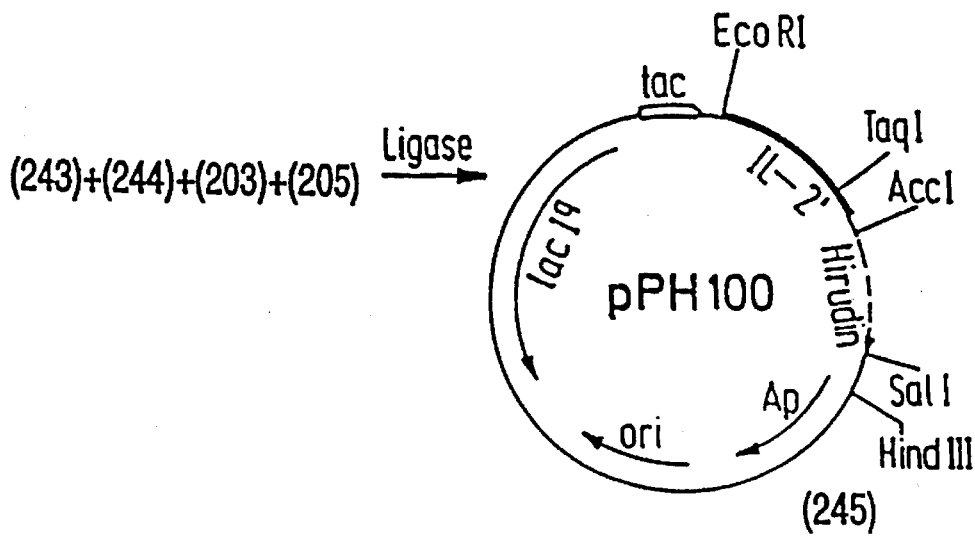

FIG. 17 relates to the synthesis of the plasmid pPH100 which codes for a fusion protein having the amino acid sequence of hirudin.

Figure 18:
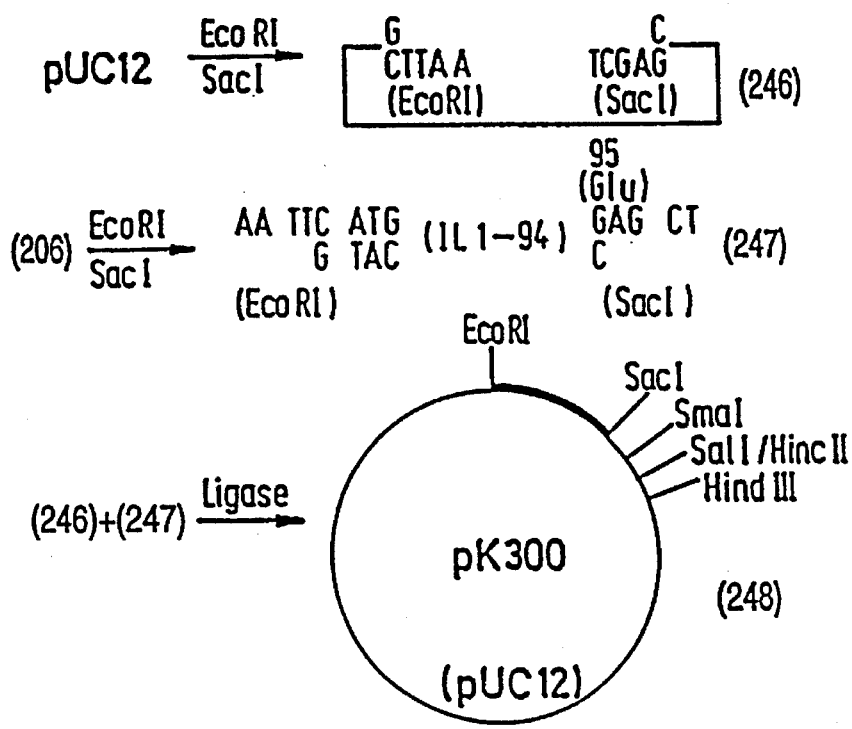
Figure 18A:
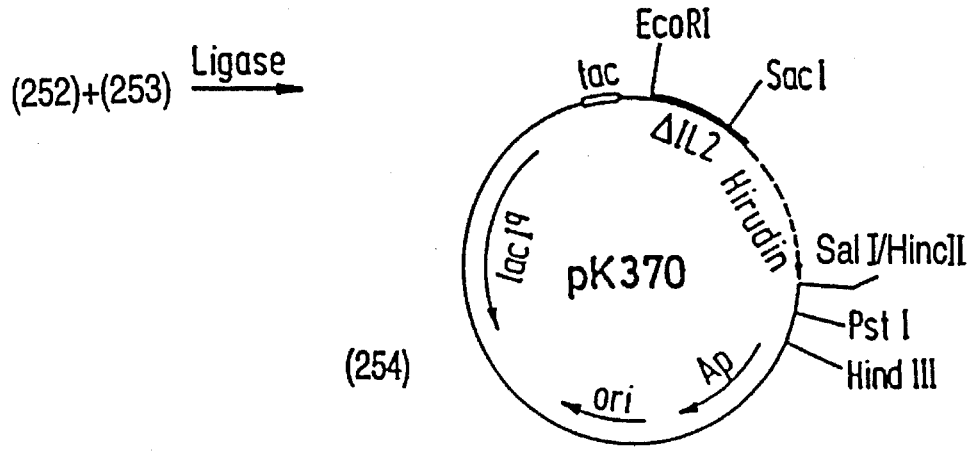

FIG. 18, and its continuation FIG. 18a, relate to the construction of the plasmid pK370 which codes for a fusion protein having the amino acid sequence of hirudin.

Figure 19:
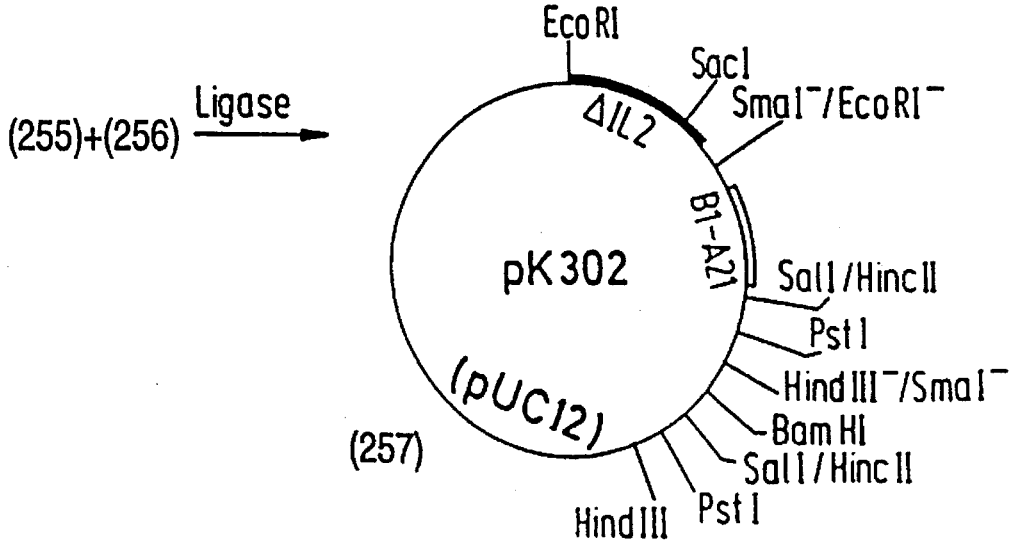
Figure 19A:
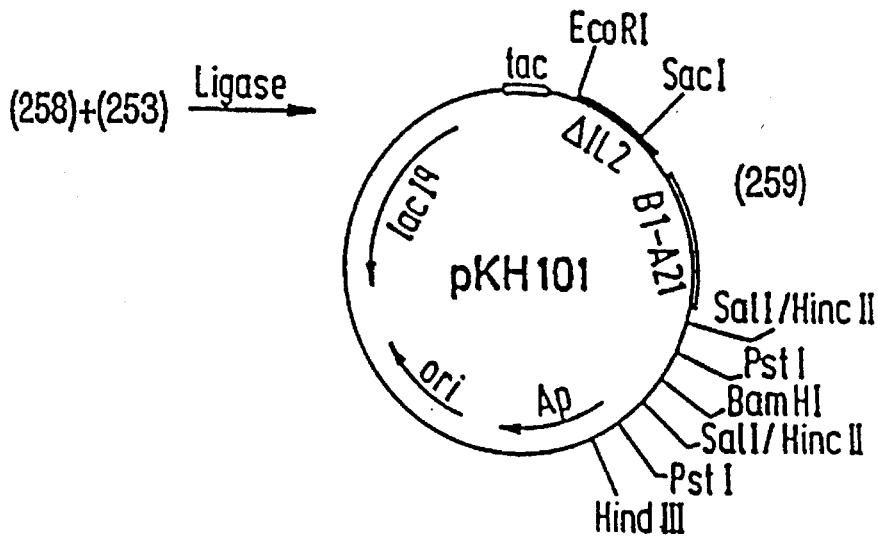

FIG. 19, and its continuation FIG. 19a, relate to the synthesis of the plasmid pKH101 which codes for a fusion protein having the amino acid sequence of monkey proinsulin.

In general, the figures are not drawn to scale; in particular, the scale has been "stretched" in depicting the polylinkers.

The invention is explained in detail in the examples which follow, in which the numbering coincides with that in the figures. Unless otherwise stated, percentage data relate to weight.

EXAMPLE A

Figure 5:
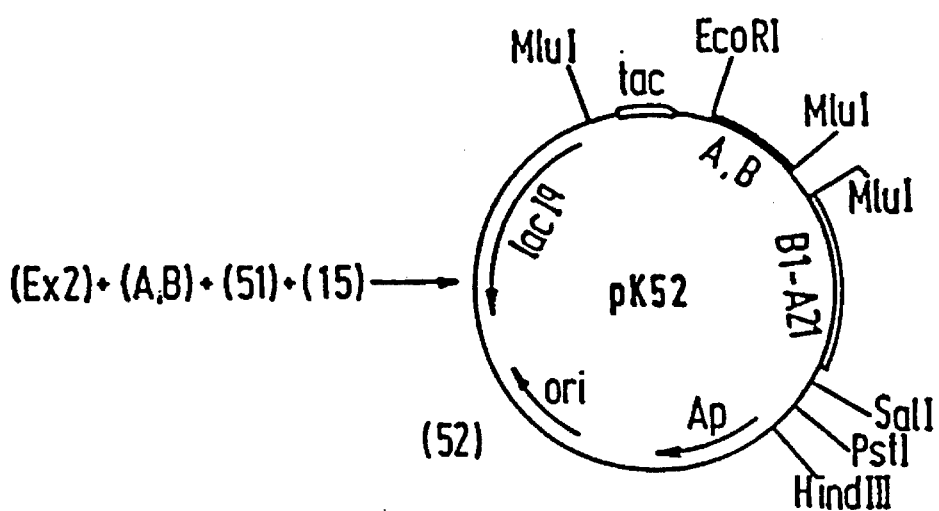
FIG. 5 shows the construction of the expression plasmid pK52 which differs from pK51 by the inserted MluI linker (51) which codes for the amino acid sequence which permits cleavage with factor Xa. pK52 can also be obtained from pK50 (FIG. 3) by cleavage with MluI and introduction of the said MluI linker.
Figure 20:
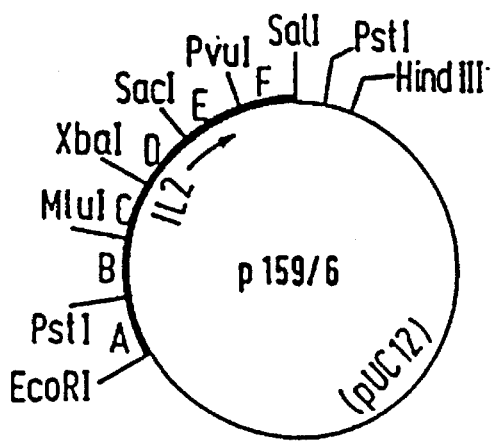
Figure 21:
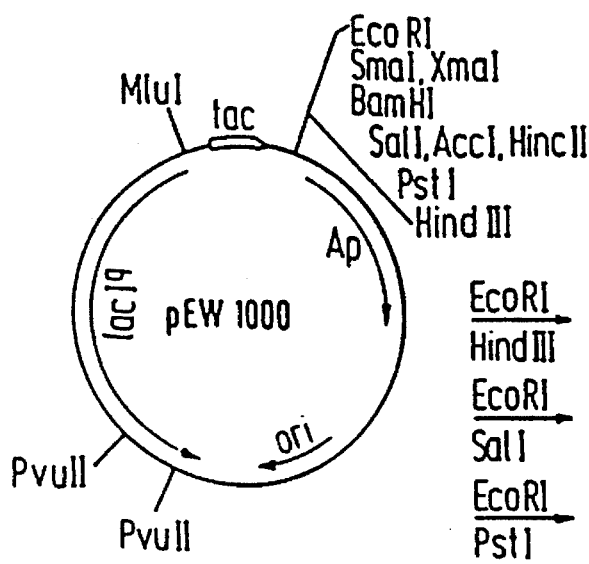
FIG. 21 shows the expression plasmid pEW1000, whose preparation is described herein and in German Patent Application P 3,541,856.7 and is shown in FIG. 14 herein and in FIG. 1 of that German Patent Application. This plasmid is opened in the polylinker sequence by appropriate double digestion, this resulting in the linearized plasmids (Ex1) to Ex4).

The starting plasmid p159/6 is described in EP-A 0,163, 249 (FIG. 5). The sequence defined there as "IL-2" or in the text as "DNA sequence I" is in FIG. 20 divided into segments A to F which are bounded by cleavage sites for the enzymes EcoRI, PstI, MluI, XbaI, SacI, PvuI and SalI. Double digestion with the appropriate enzymes results in the segments (A) to (F) or adjoined segments, for example the segment (A,B) with EcoRI and MluI.

EXAMPLE B

The preparation of the expression plasmid pEW1000 is described below (FIG. 14) and has been proposed in the (not prior-published) German Patent Application P3,541,856.7 (FIG. 1). This plasmid is a derivative of the plasmid ptac11 (Amann et al., Gene 25 (1983) 167–178) into whose recognition site for EcoRI has been incorporated a synthetic sequence which contains a SalI cleavage site. In this way, the expression plasmid pKK177.3 is obtained. Insertion of the lac repressor (Farabaugh, Nature, 274 (1978) 765–769) results in the plasmid pJF118. This is opened at the unique restriction cleavage site for AvaI, and is, in a known matter, shortened by about 1000 bp by exonuclease treatment and is ligated. This results in the plasmid pEW1000. Opening this plasmid in the polylinker sequence using the enzymes EcoRI and HindIII, SalI, PstI or SmaI results in the linearized expression plasmids (Ex1), Ex2), (Ex3) and (Ex4).

EXAMPLE C

The commercially available plasmid pUC12 is opened with EcoRI and SalI, and the linearized plasmid (1) is isolated. Ligation of (1) with the segment (A), the synthetic linker sequence (2) and the segment (F) results in the plasmid pW226 (3).

The strain E. coli 79/02 is transformed in a known manner with the plasmid DNA from the ligation mixture. The cells are plated out on agar plates which contain isopropyl-β-D-thio-galactopyranoside (IPTG), 5-bromo-4-chloro-3-indolyl-β-D-galactopyranoside (X-gal) and 20 µg/ml ampicillin (Ap). The plasmid DNA is obtained from white clones, and the formation of the plasmid (3) is confirmed by restriction analysis and DNA sequence analysis.

The small EcoRI-HindIII fragment (4) is cut out of the plasmid (3) and is isolated. This fragment is ligated with the linearized expression plasmid (Ex1) in a T4 DNA ligase reaction. The resulting plasmid pW226-1 (5) is characterized by restriction analysis.

Competent cells of the strain E. coli Mc 1061 are transformed with DNA from the plasmid pW 226-1. Clones which are resistant to ampicillin are isolated on Ap-containing agar plates. The plasmid DNA is reisolated from Mc 1061 cells and then characterized anew by restriction analysis. Competent cells of the E. coli strain W 3110 are now transformed with plasmid DNA isolated from E. coli Mc 1061 cells. E. coli W 3110 cells are always used for expression hereinafter. All the expression experiments in the stated examples are carried out in the accordance with the following conditions.

An overnight culture of E. coli cells which contain the plasmid (5) is diluted in the ratio of about 1:100 with LB medium (J. H. Miller, Experiments in Molecular Genetics, Cold Spring Harbor Laboratory, 1972) which contains 50 µg/ml ampicillin, and growth is followed by measurement of the OD. When the OD is 0.5, the culture is adjusted to 1 mM in IPTG and, after 150 to 180 minutes, the bacteria are spun down. The bacteria are boiled in a buffer mixture (7M urea, 0.1% SDS, 0.1M sodium phosphate, pH 7.0) for 5 minutes, and samples are applied to a SDS gel electrophoresis plate. After electrophoresis, bacteria which contain the plasmid (5) produce a protein band which corresponds to the size of the expected protein (6 kD).

The stated induction conditions apply to shake cultures; for larger fermentations appropriate modifications of the OD values and, where appropriate, slight variations in the IPTG concentrations are advantageous.

The resulting protein shows no biological activity in a cell proliferation test with an IL-2-dependent cell line (CTLL 2).

EXAMPLE 1

The plasmid (3) of Example C is opened with MluI and SalI, and the two resulting fragments are separated by gel electrophoresis. The larger fragment (11) is isolated. The synthetic oligonucleotide (12) is ligated with the blunt-ended DNA (13) coding for proinsulin (Wetekam et al., Gene 19 (1982) 179–183), this resulting in DNA sequence (14). The latter is cut with MluI and SalI resulting in DNA sequence (15). The latter is now ligated with the fragment (11), this resulting in formation of the plasmid pKH40 (16). The latter is characterized by restriction analysis.

The plasmid (16) is digested with EcoRI and HindIII, and the small fragment (17) is isolated by gel electrophoresis. Ligation with the linearized expression plasmid (Ex1) results in the expression plasmid pK40 (18). Expression as indicated in Example C results in a protein which, after cell disruption, is found in the soluble fraction of cellular protein. The Western blot technique is used to demonstrate that the proinsulin sequence is intact.

EXAMPLE 2

The starting material is the plasmid pPH30 which is depicted in FIG. 16c and in the (not prior-published) German Patent Application P 3,541,856.7, in FIG. 3c. Within the meaning of the present invention, the IL-2 part-sequence is shown as "A-E" (20) in FIG. 2. The end of this sequence and the bridging element up to the proinsulin sequence is shown as (20a) in FIG. 2.

The plasmid (20) is digested with PvuI and HindIII, and the small fragment (22) is isolated. In addition, the plasmid (3) is opened with EcoRI and PvuI, and the small fragment (23) is isolated. Moreover, the vector pUC12 is digested with EcoRI and HindIII, and the large fragment (21) is isolated. Ligation of the fragments (21), (23) and (22) results in the plasmid pSL11 (24).

The plasmid (24) is digested with HindIII and partially with EcoRI, and the fragment (25) which contains the segment A and the proinsulin gene is isolated. Ligation of (25) into the linearized expression plasmid (Ex1) results in the expression plasmid pSL12 (26).

Expression as indicated in Example C and subsequent working up results in a soluble fusion protein. Western blot analysis with insulin antibodies confirms that this protein contains the intact insulin sequence.

EXAMPLE 3

The plasmid ptrpED5-1 (30) (Hallewell et al., Gene 9 (1980) 27–47) is used for amplification of the proinsulin gene. The plasmid is opened with HindIII and SalI, and the large fragment (31) is isolated. The fragment (31) is ligated with DNA sequence (14), this resulting in the plasmid pH106/4 (32).

The plasmid (32) is digested with SalI and MluI, and the small fragment (15) is isolated. The linearized expression plasmid (Ex2), the segment (A,B) and the fragment (15) are now ligated, this resulting in the expression plasmid pK50 (33).

Expression of the coded fusion protein is carried out as indicated in Example C. The cells are then spun down from the culture broth and ruptured in a French press. The protein suspension is now centrifuged to separate it into its soluble and insoluble protein constituents. The two fractions are analyzed by gel electrophoresis in a known manner on 17.5% SDS polyacrylamide gels and subsequently by staining the proteins with the dyestuff Coomassie blue. It is found, surprisingly, that the fusion protein is located in the insoluble sediment. Western blot analysis with insulin antibodies confirms that intact proinsulin is present in the fusion protein.

The sediment from the French press disruption can now immediately be used further for isolation of proinsulin.

EXAMPLE 4

The starting material is the plasmid pPH20 (40) which is depicted in FIG. 16c and in the German Patent Application P 3,541,856.7, in FIG. 3c. Cutting this plasmid with EcoRI, filling in the protruding ends and cutting with HindIII results in the fragment (41), from which the DNA sequence of the part of (40) which is of interest here can be seen.

Ligation of the linearized expression plasmid (Ex4) with the segment (A,B), the synthetic oligonucleotide (42) and the fragment (41) results in the plasmid pK51 (43).

EXAMPLE 5

Ligation of the linearized expression plasmid (Ex2) with the segment (A,B), the synthetic oligonucleotide (51) and the DNA sequence (15) results in the plasmid pK52 (52). The correct orientation of the oligonucleotide (51) is established by sequence analysis. The plasmid codes for a fusion protein which contains the amino acid sequence which corresponds to the oligonucleotide (51) and thus can be cleaved by activated Factor Xa.

The plasmid (52) can also be obtained in the following manner:

Partial cutting of the plasmid (33) with MluI and ligation of the resulting opened plasmid (53) with the DNA sequence (51) likewise results in the plasmid pK52.

EXAMPLE 6

Partial cutting of the plasmid (43) with MluI and ligation of the resulting linearized plasmid (61) with the synthetic DNA sequence (51) results in the plasmid pK53 (62). The latter likewise codes for a fusion protein which can be cleaved with activated factor Xa. The correct orientation of the sequence (51) is established, as in Example 5, by DNA sequence analysis.

EXAMPLE 7

The plasmid (26) is cleaved with XbaI and partially with MluI, and the large fragment (71) is isolated. Ligation with the segment (C) results in the plasmid pSL14 (72). After expression and cell disruption, the fusion protein is found in the soluble fraction of cellular protein.

EXAMPLE 8

The plasmid (20) is cleaved with XbaI and partially with EcoRI, and the protruding ends are filled in, this resulting in DNA sequence (81). Ligation under blunt end conditions resulting in the plasmid pPH31 (82). The fusion protein is found in the insoluble fraction of cellular protein.

EXAMPLE 9

The starting material used is the plasmid (90) which is described in EP-A 0,171,024 (FIG. 3). This plasmid is reacted with SalI and then with AccI, and the small fragment (91) is isolated. The latter is ligated with the synthetic oligonucleotide (92), this resulting in DNA sequence (93). The latter is cut with MluI, this resulting in DNA fragment (94).

The plasmid (33) is digested with MluI, partially, and with SalI, and the large fragment (95) is isolated. The latter is ligated with the DNA sequence (94), this resulting in the expression plasmid pK192 (96). The latter codes for a fusion protein in which the first 38 amino acids of IL-2 are followed by methionine and then by the amino acid sequence of hirudin. The fusion protein is found in the soluble fraction of cellular protein.

EXAMPLE 10

The starting material used is the plasmid pHG23 (100) which is described in EP-A 0,183,350 and which is generally accessible from the American Type Culture Collection under No. ATCC 39000. This plasmid is cut with SfaNI, the protruding ends are filled in, then reaction with PstI is carried out, and the small fragment (101) is isolated. Ligation of the linearized expression plasmid (Ex3) with the segment (A, B), the synthetic oligonucleotide (102) and the fragment (101) results in the expression plasmid pW214 (103). This plasmid codes for a fusion protein in which the first 38 amino acids of IL-2 are followed by the sequence which is derived from the oligonucleotide (102) and which allows the molecule to be cleaved with factor Xa, with subsequently the amino acid sequence of CSF. After cell disruption, the fusion protein is found in the insoluble fraction of cellular protein.

EXAMPLE 11

The starting plasmid pW216 (110) is proposed in German Patent Application P 3,545,568.3 (FIG. 2b). In this plasmid, the IL-2 sequence corresponding to segments A to E (PvuI cleavage site) is followed by a linker which codes for the amino acids Asp-Asp-Pro, immediately followed by the amino acid sequence for CSF. The connecting sequence between IL-2 and CSF allows the fusion protein to be cleaved proteolytically.

The sequence (111) is isolated from the plasmid (110) by cutting with PvuI and HindIII.

The plasmid (3) is cut with MluI and XbaI, and the large fragment (112) is isolated. The latter is ligated with the segment (C), this resulting in the plasmid pW227 (113). This plasmid is reacted with EcoRI and HindIII, and the short fragment (114) is isolated. If this fragment is ligated with the linearized expression plasmid (Ex1) the result is the plasmid pW227-1 (115). The plasmid codes for a protein which is derived from IL-2 but which has no IL-2 activity.

The plasmid (113) is additionally cut with EcoRI and PvuI, and the short fragment (116) is isolated. Ligation of the linearized expression plasmid (Ex1) with the fragments (116) and (111) results in the expression plasmid pW233 (117). The latter codes for an insoluble fusion protein which, by reason of the abovementioned linker, can be cleaved proteolytically.

EXAMPLE 12

The plasmid (3) is cut with XbaI and SacI, and the large fragment (121) is isolated. Ligation with the segment (D) results in the plasmid pW228 (122). The latter is cut with EcoRI and Hind III, and the small fragment (123) is isolated. Ligation of the linearized expression plasmid (Ex1) with the fragment (123) results in the expression plasmid pW228-1 (124). This plasmid codes for a biologically inactive IL-2 derivative. The plasmid is digested with EcoRI and PvuI, and the short fragment (125) is isolated. Ligation of the linearized expression plasmid (Ex1) with the fragments (125) and (111) results in the expression plasmid pW234 (126). The latter codes for a sparingly soluble fusion protein which can likewise be cleaved proteolytically.

EXAMPLE 13

For the construction of plasmids which are suitable, in particular, for the expression of cDNA sequences, initially the polylinker sequence (131) is synthesized.

Ligation of the linearized plasmid (1) with the segment (A), the polylinker sequence (131) and segment (F) results in the plasmid pH200 (132).

The plasmid (132) is reacted with EcoRI and MluI, and the large fragment (133) is isolated. Ligation of the latter with the segment (A,B) results in the plasmid pH201 (134).

The plasmid (134) is reacted with EcoRI and HindIII, and the short fragment (135) is isolated. Ligation of this fragment with the linearized expression plasmid (Ex1) results in the expression plasmid pH 202 (136).

The plasmid (136) is opened with BamHI, and the cDNA which is to be expressed is introduced into the linearized plasmid via a commercially available BamHI adaptor. Depending on the orientation of the cDNA, every third sequence is attached to (A,B) in the reading frame. If the cDNA sequence contains no stop codon, the polypeptide sequence for which it codes is additionally protected by the amino acid sequence corresponding to the segment (F).

If the cDNA is not connected in the correct reading frame, a shift of the reading frame is brought about by, for example, cleaving the cDNA-containing (original or multiplied) plasmids with MluI or XbaI (as long as the cDNA does not contain cleavage sites for these enzymes) and filling in the protruding ends by a Klenow polymerase reaction.

EXAMPLE 14

Figure 6:
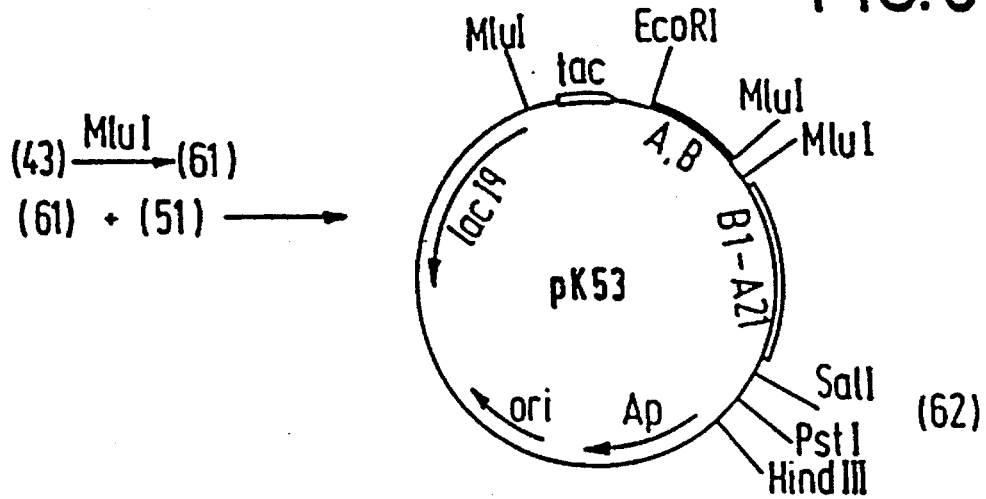
FIG. 6 shows the construction of the expression plasmid pK53 from pK51 (FIG. 4), likewise by introduction of the MluI linker.

The plasmid pJF118 (201) is obtained by insertion of the lac repressor (P. J. Farabaugh, Nature, 274 (1978) 765-769) into the plasmid pKK 177-3 (Amann et al., Gene, 25 (1983) 167) (FIG. 14), (cf. German Patent Application P 35 26 995.2, Example 6, FIG. 6). pJF118 is opened at the unique restriction site for AvaI and is shortened by about 1,000 bp in a manner known per se by exonuclease treatment. Ligation results in the plasmid pEW 1000 (202) (FIG. 14) in which the lac repressor gene is fully retained but which, by reasons of the shortening, is present in a distinctly higher copy number than the starting plasmid.

In place of the plasmid pKK177-3, it is also possible to start from the abovementioned commercially available plasmid pKK223-3, to incorporate the lac repressor, and to shorten the resulting product analogously.

The plasmid pEW 1000 (202) is opened with the restriction enzymes EcoRI and SalI (203).

The plasmid (204) (FIG. 14) which codes for hirudin and has been prepared as in Example 4 (FIG. 3) of German Offenlegungsschrift 3,429,430 (European Patent Application 0,171,024), is opened with the restriction enzymes AccI and SalI, and the small fragment (205) which mostly contains the hirudin sequence is isolated.

The plasmid p159/6 (206), prepared as in Example 4 (FIG. 5) of German Offenlegungsschrift 3,419,995 (European Patent Application 0,163,249), is opened with the restriction enzymes EcoRI and PvuI, and the small fragment (207) which contains most of the IL-2 sequence is isolated. This part-sequence and other shortened IL-2 sequences in the text which follows are identified by "ΔIL2" in the figures.

Thereafter, the sequences (203), (205), (207) and the synthetic DNA sequence (208) (FIG. 14a) are treated with T4 ligase. The plasmid pK360 (209) is obtained.

Competent *E. coli* cells are transformed with the ligation product and plated out on NA plates which contain 25 µg/ml ampicillin. The plasmid DNA of the clones is characterized by restriction and sequence analysis.

An overnight culture of *E. coli* cells which contain the plasmid (209) is diluted in the ratio of approximately 1:100 with LB medium (J. H. Miller, Experiments in Molecular Genetics, Cold Spring Harbor Laboratory, 1972) which contains 50 µg/ml ampicillin, and the growth is monitored by measurement of the OD. When the OD is 0.5, the shake culture is adjusted to 1 mM isopropyl-β-galactopyranoside (IPTG) and, after 150 to 180 minutes, the bacteria are spun down. The bacteria are boiled in a buffer mixture (7M urea, 0.1% SDS, 0.1M sodium phosphate, pH 7.0) for 5 minutes, and samples are applied to a SDS gel electrophoresis plate. Bacteria which contain the plasmid (209) provide, after electrophoresis, a protein band which corresponds to the size of the expected fusion protein.

Disruption of the bacteria (French Press; DYNO MILL®) and centrifugation results in the fusion protein being located in the sediment so that considerable amounts of the other proteins can now be removed with the supernatant. After isolation of the fusion protein, cleavage with cyanogen bromide results in liberation of the expected hirudin peptide. The latter is characterized after isolation by protein in sequence analysis.

The indicated induction conditions apply to shake cultures; with larger fermentations, appropriately modified OD values, and where appropriate, slight changes in the IPTG concentrations are expedient.

EXAMPLE 15

The plasmid (204) (FIG. 14) is opened with AccI, and the protruding ends are filled in with Klenow polymerase. Then cleavage with SacI is carried out, and the fragment (210) which contains most of the hirudin sequence is isolated (FIG. 15).

The commercially available vector pUC 13 is opened with the restriction enzymes SacI and SmaI, and the large fragment (211) is isolated.

Using T4 ligase, the fragments (210) and (211) are now ligated to give the plasmid pK 400 (212) (FIG. 15). The plasmid (12) is shown twice in FIG. 15, the lower representation emphasizing the amino acid sequence of the hirudin derivative which can thus be obtained.

The plasmid (204) (FIG. 14) is opened with the restriction enzymes KpnI and SalI, and the small fragment (213) which contains the hirudin part-sequence is isolated (FIG. 15a).

The plasmid (212) (FIG. 14a) is reacted with the restriction enzymes Hinc II and KpnI, and the small fragment (214) which contains the hirudin part-sequence is isolated (FIG. 5a).

The plasmid (209) (FIG. 14a) is partially cleaved with EcoRI, the free ends are subjected to a fill-in reaction with Klenow polymerase, and SalI cleavage is carried out. The derivative (215) of the plasmid pK360 is obtained (FIG. 15a).

Ligation of the fragments (203), (213), (214) and (215) results in the plasmid pK410 (216) which is shown twice in FIG. 15a, the lower representation showing the amino acid sequence of the fusion protein and thus that of the hirudin derivative obtained after acid cleavage.

Expression and working up as in Example 14 results in a new hirudin derivative which has the amino acids proline and histidine in positions 1 and 2. This hirudin derivative has the same activity as the natural product, according to German Offenlegungsschrift 3,429,430, which has the amino acids threonine and tyrosine in these positions, but is more stable to attack by aminopeptidases, which may result in advantages for in vivo use.

EXAMPLE 16

The commercially available vector pBR 322 is opened with BamHI, this resulting in the linearized plasmid (217) (FIG. 16). The free ends are partially filled in by use of dATP, dGTP and dTTP, and the protruding nucleotide G is split off with S1 nuclease, this resulting in the pBR 322 derivative (218).

The HaeIII fragment (219) from monkey proinsulin (Wetekam et al., Gene, 19 (1982) 181) is ligated with the modified plasmid (218), this resulting in the plasmid pPH 1 (220). Since the insulin part-sequence has been inserted into the tetracycline resistance gene, the clones which contain this plasmid are not resistant to tetracycline and thus can be identified.

The plasmid (220) is opened with BamHI and DdeI, and the small fragment (221) is isolated. In addition, the DdeI-PvuII part-sequence (222) from the monkey proinsulin sequence is isolated.

The vector pBR 322 is opened with BamHI and PvuII, and the linearized plasmid (223) is isolated.

Ligation of the insulin part-sequences (221) and (222) with the opened plasmid (223) results in the plasmid pPH5 (224) (FIG. 16a). The latter is opened with BamHI and PvuII, and the small fragment (225) is isolated.

The DNA sequence (226) to make up the insulin structure is synthesized.

The commercially available vector pUC 8 is opened with the enzymes BamHI and SalI, and the remainder of the plasmid (227) is isolated. The latter is ligated with the DNA sequences (225) and (226) to give the plasmid pPH 15 (228). The latter is opened with SalI and the protruding ends are filled in (FIG. 16b). Bam HI is used to cleave the DNA sequence (230) off the resulting plasmid derivative (229).

The commercially available vector pUC 9 is opened with the enzymes BamHI and SmaI, and the large fragment (231) is isolated. The latter is ligated with the DNA sequence (230), this resulting in the plasmid pPH16 (232).

The plasmid (232) is opened with SalI, and the linearized plasmid (233) is partially filled in with dCTP, dGTP and dTTP, and the remaining nucleotide T is cleaved off with S1 nuclease. The resulting plasmid derivative (234) is treated with BamHI, and the protruding single strand is removed from the product (235) with S1 nuclease, this resulting in the plasmid derivative (236).

The blunt ends of the plasmid derivative (236) are cyclized to give the plasmid pPH 20 (237) (FIG. 16c).

Competent *E. coli* Hb 101 cells are transformed with the ligation mixture and plated out on selective medium. Clones which contain the desired plasmid express proinsulin, and 28 of 70 clones tested radioimmunologically contained detectable proinsulin. The plasmids are also characterized by DNA sequence analysis. They contain DNA which codes for arginine upstream of the codon for the first amino acid of the B chain (Phe).

The plasmid (237) is cleaved with HindIII, the protruding ends are filled in, and then cleavage with DdeI is carried out. The small fragment (238) is isolated.

The plasmid (228) (FIG. 16a) is cleaved with SalI and DdeI, and the small fragment (239) is separated off.

The plasmid 209 (FIG. 14a) is initially cleaved with AccI, the free ends are filled in, and then partial cleavage with EcoRI is carried out. The fragment (240) which contains the shortened IL-2 sequence is isolated.

The linearized plasmid (203) (FIG. 14) and the DNA segments (238), (239) and (240) are now ligated to give the plasmid pPH 30 (241). This plasmid codes for a fusion protein which has, downstream of amino acids 1 to 114 of IL-2, the following amino acid sequence:

Asp-Phe-Met-Ile-Thr-Thr-Tyr-Ser-Leu-Ala-Ala-Gly-Arg.

The arginine which is the last amino acid in this bridging element Y makes it possible to cleave off the insulin chains with trypsin.

It is also possible starting from plasmid (209) (FIG. 14a) to obtain plasmid (241) by the following route:

Plasmid (209) is opened with AccI, the protruding ends are filled in, then cleavage with SalI is carried out, and the resulting plasmid derivative (242) is ligated with the segments (203), (238) and (239).

EXAMPLE 17

The plasmid (206) (FIG. 14) is opened with the restriction enzymes TaqI and EcoRI, and the small fragment (243) is isolated (FIG. 17). This fragment is ligated with the synthesized DNA sequence (244) and the segments (203) and (205) to give the plasmid pPH 100 (245). This plasmid codes for a fusion protein in which the first 132 amino acids of IL-2 are followed by the bridging element Asp-Pro and then by the amino acid sequence of hirudin. Thus, proteolytic cleavage provides a modified, biologically active IL-2' which contains Asp in place of Thr in position 133, and a hirudin derivative which contains an N-terminal Pro upstream of the amino acid sequence of the natural product. This product is also biologically active and, compared with the natural product, is more stable to attack by proteases.

The IL-2' hirudin fusion protein also has biological activity. Biological activity was found in a cell proliferation test using an IL-2-dependent cell line (CTLL2).

Furthermore, after denaturation in 6M guanidinum hydrochloride solution, followed by renaturation in buffer solution (10 mM tris-HCl, pH 8.5, 1 mM EDTA), high IL-2 activity was found. In addition, the coagulation time of acid-treated blood to which thrombin had been added was increased after addition of the fusion protein. Thus a bifunctional fusion protein is obtained.

EXAMPLE 18

The commercially available vector pUC 12 is opened with the restriction enzymes EcoRI and SacI (FIG. 18). Into this linearized plasmid (246) is inserted an IL-2 part-sequence which has been cleaved out of the plasmid (206) (FIG. 14) with the restriction enzymes EcoRI and SacI. This sequence (247) comprises the complete triplets for the first 94 amino acids of IL-2. Ligation of (246) and (247) results in the plasmid pK 300 (248).

The plasmid (209) (FIG. 14a) is opened with EcoRI, the protruding ends are filled in, and then cleavage with HindIII is carried out. The small fragment (249) which contains part of the polylinker from pUC 12 downstream of the DNA sequence coding for hirudin is isolated.

The plasmid (248) is opened with the restrictive enzymes SmaI and HindIII, and the large fragment (250) is isolated. Ligation of (250) with (249) results in the plasmid pK 301 (251).

The ligation mixture is used to transform E. coli 294 cells. Clones which contain the plasmid (251) are characterized by restriction analysis. They contain DNA in which the codons for the first 96 amino acids of IL-2 are followed by codons for a bridging element of 6 amino acids and, thereafter, the codons for hirudin.

The plasmid (251) is reacted with EcoRI and HindIII, and the fragment (252) which contains the DNA sequence for the eukaryotic fusion protein is isolated (FIG. 18a).

The plasmid (202) (FIG. 14) is opened with EcoRI and Hind III. The resulting linearized plasmid (253) is ligated with the DNA sentence (252), this resulting in the plasmid pk 370 (254).

When expression of the plasmid (254) is effected in E. coli as in Example 14, the fusion protein obtained has the first 96 amino acids of IL-2 followed by the bridging element:

Ala-Gln-Phe-Met-Ile-Thr and, thereafter, the amino acid sequence of hirudin.

EXAMPLE 19

Using the restriction enzymes EcoRI and HindIII, the DNA segment which codes for monkey proinsulin is cleaved out of the plasmid (241) (Example 16; FIG. 16c), and the protruding ends are filled in (FIG. 19). The DNA segment (755) is obtained.

The plasmid (248) (Example 18; FIG. 18) is opened with Sma I and treated with bovine alkaline phosphatase. The resulting linearized plasmid (256) is ligated with the DNA segment (255), this resulting in the plasmid pK 302 (257). E. coli 294 cells are transformed with the ligation mixture, and clones containing the desired plasmid are characterized first by restriction analysis and then by sequence analysis of the plasmid DNA.

Using EcoRI and HindIII, the segment (258) which codes for IL-2 and monkey proinsulin is cleaved out of the plasmid (257) (FIG. 19a).

The plasmid (202) (Example 14; FIG. 14) is likewise cleaved with EcoRI and HindIII to obtain plasmid (253) (Example 18; FIG. 18a) and the segment (258) is ligated into the linearized plasmid (253). The plasmid pKH 101 (259) is obtained.

Expression as in Example 14 results in a fusion protein in which the first 96 amino acids of IL-2 are followed by a bridging element of 14 amino acids (corresponding to Y in DNA segment (258), which is followed by the amino acid sequence of monkey proinsulin.

TABLE I

| DNA sequence of interleukin-2 | | | | | | | | | |
|---|---|---|---|---|---|---|---|---|---|
| Triplet No. | | | | | | 0 | 1 | 2 | |
| Amino acid | | | | | | Met | Ala | Pro | |
| Nucleotide No. | | | 1 | | | | 10 | | |
| Cod. strand | | 5' | AA | | TTC | ATG | GCG | CCG | |
| Non-cod. strand | | 3' | | | G TAC | | CGC | GGC | |
| | | | | | (EcoRI) | | | | |
| 3 | 4 | 5 | 6 | 7 | 8 | 9 | 10 | 11 | 12 |
| Thr | Ser | Ser | Ser | Thr | Lys | Lys | Thr | Gln | Leu |
| | 20 | | | | 30 | | | 40 | |
| ACC | TCT | TCT | TCT | ACC | AAA | AAG | ACT | CAA | CTG |
| TGG | AGA | AGA | AGA | TGG | TTT | TTC | TGA | GTT | GAC |

TABLE I-continued

DNA sequence of interleukin-2

| 13 | 14 | 15 | 16 | 17 | 18 | 19 | 20 | 21 | 22 |
|---|---|---|---|---|---|---|---|---|---|
| Gln | Leu 50 | Glu | His | Leu | Leu 60 | Leu | Asp | Leu 70 | Gln |
| CAA | CTG | GAA | CAC | CTG | CTG | CTG | GAC | CTG | CAG |
| GTT | GAC | CTT | GTG | GAC | GAC | GAC | CTG | GAC | GTC |
|  |  |  |  |  |  |  |  | PstI |  |
| 23 | 24 | 25 | 26 | 27 | 28 | 29 | 30 | 31 | 32 |
| Met | Ile 80 | Leu | Asn | Gly | Ile 90 | Asn | Asn | Tyr 100 | Lys |
| ATG | ATC | CTG | AAC | GGT | ATC | AAC | AAC | TAC | AAA |
| TAC | TAG | GAC | TTG | CCA | TAG | TTG | TTG | ATG | TTT |
| 33 | 34 | 35 | 36 | 37 | 38 | 39 | 40 | 41 | 42 |
| Asn | Pro 110 | Lys | Leu | Thr | Arg 120 | Met | Leu | Thr 130 | Phe |
| AAC | CCG | AAA | CTG | ACG | CGT | ATG | CTG | ACC | TTC |
| TTG | GGC | TTT | GAC | TGC | GCA | TAC | GAC | TGG | AAG |
|  |  |  |  | MluI |  |  |  |  |  |
| 43 | 44 | 45 | 46 | 47 | 48 | 49 | 50 | 51 | 52 |
| Lys | Phe 140 | Tyr | Met | Pro | Lys 150 | Lys | Ala | Thr 160 | Glu |
| AAA | TTC | TAC | ATG | CCG | AAA | AAA | GCT | ACC | GAA |
| TTT | AAG | ATG | TAC | GGC | TTT | TTT | CGA | TGG | CTT |
| 53 | 54 | 55 | 56 | 57 | 58 | 59 | 60 | 61 | 62 |
| Leu | Lys 170 | His | Leu | Gln | Cys 180 | Leu | Glu | Glu 190 | Glu |
| CTG | AAA | CAC | CTC | CAG | TGT | CTA | GAA | GAA | GAG |
| GAC | TTT | GTG | GAG | GTC | ACA | GAT | CTT | CTT | CTC |
|  |  |  |  |  |  | XbaI |  |  |  |
| 63 | 64 | 65 | 66 | 67 | 68 | 69 | 70 | 71 | 72 |
| Leu | Lys 200 | Pro | Leu | Glu | Glu 210 | Val | Leu | Asn 220 | Leu |
| CTG | AAA | CCG | CTG | GAG | GAA | GTT | CTG | AAC | CTG |
| GAC | TTT | GGC | GAC | CTC | CTT | CAA | GAC | TTG | GAC |
| 73 | 74 | 75 | 76 | 77 | 78 | 79 | 80 | 81 | 82 |
| Ala | Gln 230 | Ser | Lys | Asn | Phe 240 | His | Leu | Arg 250 | Pro |
| GCT | CAG | TCT | AAA | AAT | TTC | CAC | CTG | CGT | CCG |
| CGA | GTC | AGA | TTT | TTA | AAG | GTG | GAC | GCA | GGC |
| 83 | 84 | 85 | 86 | 87 | 88 | 89 | 90 | 91 | 92 |
| Arg | Asp 260 | Leu | Ile | Ser | Asn 270 | Ile | Asn | Val 280 | Ile |
| CGT | GAC | CTG | ATC | TCT | AAC | ATC | AAC | GTT | ATC |
| GCA | CTG | GAC | TAG | AGA | TTG | TAG | TTG | CAA | TAG |
| 93 | 94 | 95 | 96 | 97 | 98 | 99 | 100 | 101 | 102 |
| Val | Leu 290 | Glu | Leu | Lys | Gly 300 | Ser | Glu | Thr 310 | Thr |
| GTT | CTG | GAG | CTC | AAA | GGT | TCT | GAA | ACC | ACG |
| CAA | GAC | CTC | GAG | TTT | CCA | AGA | CTT | TGG | TGC |
|  |  | SacI |  |  |  |  |  |  |  |
| 103 | 104 | 105 | 106 | 107 | 108 | 109 | 110 | 111 | 112 |
| Phe | Met 320 | Cys | Glu | Tyr | Ala 330 | Asp | Glu | Thr 340 | Ala |
| TTC | ATG | TGC | GAA | TAC | GCG | GAC | GAA | ACT | GCG |
| AAG | TAC | ACG | CTT | ATG | CGC | CTG | CTT | TGA | CGC |
| 113 | 114 | 115 | 116 | 117 | 118 | 119 | 120 | 121 | 122 |
| Thr | Ile 350 | Val | Glu | Phe | Leu 360 | Asn | Arg | Trp 370 | Ile |
| ACG | ATC | GTT | GAA | TTT | CTG | AAC | CGT | TGG | ATC |
| TGC | TAG | CAA | CTT | AAA | GAC | TTG | GCA | ACC | TAG |
| PvuI |  |  |  |  |  |  |  |  |  |
| 123 | 124 | 125 | 126 | 127 | 128 | 129 | 130 | 131 | 132 |
| Thr | Phe 380 | Cys | Gln | Ser | Ile 390 | Ile | Ser | Thr 400 | Leu |
| ACC | TTC | TGC | CAG | TCG | ATC | ATC | TCT | ACC | CTG |
| TGG | AAG | ACG | GTC | AGC | TAG | TAG | AGA | TGG | GAC |
| 133 | 134 | 135 |  |  |  |  |  |  |  |
| Thr |  | 410 |  |  |  |  |  |  |  |
| ACC | TGA | TAG |  |  |  |  |  | 3' |  |
| TGG | ACT | ATC | AGC | T |  |  |  | 5' |  |
|  |  | (SalI) |  |  |  |  |  |  |  |

What is claimed is:

1. A fusion protein comprising a ballast portion and a desired protein, said ballast portion forming the N-terminus of the fusion protein and said ballast portion consisting essentially of residues of the amino acid sequence of interleukin-2 (IL-2), wherein said ballast portion contains at least a 22-residue amino acid sequence of IL-2 and lacks IL-2 biological activity in the T-cell proliferation test.

2. A fusion protein as claimed in claim 1, wherein said amino acid sequence corresponds to that of human IL-2.

3. A fusion protein as claimed in claim 2, wherein the DNA sequence coding for said amino acid sequence of IL-2 is selected from the DNA sequence of Table I.

4. A fusion protein as claimed in claim 3, wherein said DNA sequence coding for said amino acid sequence of IL-2 consists essentially of any number of the segments A to F defined by the restriction enzyme sites of the IL-2 gene as follows:

(EcoRI)-A-PstI-B-MluI-C-XbaI-D-SacI-E-PvuI-F-(SalI)

said segments being linked together in any sequence.

5. A fusion protein as claimed in claim 1, having the formula:

$$Met-X-Y-Z \quad (Ia)$$

in which
X denotes said ballast portion;
Y denotes a direct bond or a bridging element which is composed of genetically codable amino acids and which allows the amino acid sequence to be cleaved off; and
Z is a desired protein.

6. A fusion protein as claimed in claim 5, wherein Y comprises Asp-Pro or Ile-Glu-Gly-Arg at its C-terminal end.

7. A fusion protein as claimed in claim 5, wherein Z is a sequence of proinsulin.

8. A fusion protein as claimed in claim 5 wherein Z is a sequence of hirudin that has hirudin activity.

9. A fusion protein as claimed in claim 1 wherein said desired protein is proinsulin, GM-CSF or hirudin.

10. A fusion protein as claimed in claim 1 wherein said proinsulin is monkey proinsulin or a precursor to mature insulin having the sequence of mature human insulin, or wherein said GM-CSF is human GM-CSF.

* * * * *